US012078580B2

(12) United States Patent
Nze et al.

(10) Patent No.: US 12,078,580 B2
(45) Date of Patent: Sep. 3, 2024

(54) HYDRODYNAMIC CAVITATION

(71) Applicant: UNIVERSITY OF UTAH RESEARCH FOUNDATION, Salt Lake City, UT (US)

(72) Inventors: Ugochukwu Chinedu Nze, Carson, CA (US); Himanshu Jayant Sant, Salt Lake City, UT (US); Bruce Kent Gale, Taylorsville, UT (US); Christopher J. Lambert, Salt Lake City, UT (US); Dhruv Patel, Patan (IN); Michael Beeman, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 508 days.

(21) Appl. No.: 16/803,984

(22) Filed: Feb. 27, 2020

(65) Prior Publication Data
US 2020/0271555 A1 Aug. 27, 2020

Related U.S. Application Data

(60) Provisional application No. 62/811,499, filed on Feb. 27, 2019.

(51) Int. Cl.
*G01N 1/34* (2006.01)
*G01N 1/40* (2006.01)
*G01N 33/02* (2006.01)
(52) U.S. Cl.
CPC .............. *G01N 1/34* (2013.01); *G01N 1/4077* (2013.01); *G01N 33/02* (2013.01); *G01N 2001/4088* (2013.01)

(58) Field of Classification Search
None
See application file for complete search history.

(56) References Cited

U.S. PATENT DOCUMENTS

2010/0068706 A1\* 3/2010 Pourahmadi ........... B01D 15/00
435/6.19
2016/0251703 A1\* 9/2016 Gilboa-Geffen ... C12N 15/1048
506/1

OTHER PUBLICATIONS

G. Loraine, G. Chahine, C. T. Hsiao, J. K. Choi and P. Aley, "Disinfection of gram-negative and gram-positive bacteria using DynaJets® hydrodynamic cavitating jets," Ultrasonics Sonochemistry, vol. 19, pp. 710-717, 2012. (Year: 2012).\*

(Continued)

*Primary Examiner* — Matthew D Krcha
(74) *Attorney, Agent, or Firm* — Workman Nydegger

(57) ABSTRACT

Sample preparation can include obtaining a sample in the form of a liquid mixture and forcing the liquid mixture through a cavitation chamber at an optimal pressure for separating pathogens from particles in the mixture without fragmenting at least 30% of the pathogens. Apparatuses used for sample preparation methods can include a fluid circuit, a cavitation chamber incorporated into the fluid circuit and having a channel with first, second, and third cross-sectional areas, the second cross-sectional area being downstream of and smaller than the first cross-sectional with respect to fluid flow through the fluid circuit and the third cross-sectional area being larger than and downstream of the second cross-sectional area with respect to fluid flow through the fluid circuit. The apparatus can include a pump in fluid communication with the cavitation chamber and a pressure sensor positioned upstream of the cavitation chamber.

23 Claims, 9 Drawing Sheets
(5 of 9 Drawing Sheet(s) Filed in Color)

(56) References Cited

OTHER PUBLICATIONS

A. Berceau, T. Crouse, J. Fawson, J. Hanson, Z. Kelly, A. Schwab and U. d. o. D. H. J. Sant, "Automated Stem Cell Separation," University of Utah, SLC, UT, 2016. (Year: 2016).*

M. P. Lutolf, P. M. Gilbert and H. M. Blau, "Designing materials to direct stem-cell fate," Nature, No. 462, pp. 433-441, 2009.

J. M. Gimble, A. J. Katz and B. A. Bunnell, "Adipose-Derived Stem Cells for Regenerative Medicine," Cirtulation Research, No. 100, pp. 1249-1260, 2007.

E. Oberbauer, C. Steffenhagen, C. Wurzer, C. Gabriel, H. Redl and S. Wolbank, 27 "Enzymatic and non-enzymatic isolation systems for adipose tissue-derived cells: current state of the art," Cell Regeneration, vol. 4, No. 7, 2015.

A. Dicker, K. Le Blanc, G. Astrom, V. van Harmelen, C. Gotherstrom, L. Blomqvist, P. Arner and M. Ryden, "Functional studies of mesenchymal stem cells derived from adult human adipose tissue," Experimental Cell Research, vol. 308, No. 2, pp. 283-290, 2005.

P. A. Zuk, M. Zhu, P. Ashjian, D. A. De Ugarte, J. I. Huang, H. Mizuno, Z. C. Alfonso, J. K. Fraser, P. Benhaim and M. H. Hedrick, "Human Adipose Tissue Tissue Is a Source of Multipotent Stem Cells," Molecular Biology of the Cell, vol. 13, No. 12, pp. 4279-4295, 2002.

A. Berceau, T. Crouse, J. Fawson, J. Hanson, Z. Kelly, A. Schwab and U. d. o. D. H. J. Sant, "Automated Stem Cell Separation," University of Utah, SLC, UT, 2016.

J. Katz, "Noise in the Operating Room," Anethesiology, vol. 121, pp. 894-898, 2014.

K. Yoshimura, T. Shigeura, D. Matsumoto and K. Gonda, "Charactera-tion of freshly isolated and cultured cells derived from the fatty and fluid portions of liposuction aspirates," Journal of Cellular Physi-ology, No. 208, pp. 64-76, 2006.

W. Wagner, F. Wein, A. Seckinger, N. Franhauser, U. Wirkner, U. Krause, J. Blake, C. Schwager, V. Eckstein, W. Ansorge and A. D. Ho, "Comparative characteristic of mesenchymal stem cells from human bone marrow, adipose tissue, and umbilical cord blood," ISEH Experimental Hematoloty, vol. 33, No. 11, pp. 1402-1416, 2005.

B. Lindroos, R. Suuronene and S. Miettinene, "The Potential of Adipose Stem Cells in Regenerative Medicine," Stem Cell Reviews and Reports, vol. 7, No. 2, pp. 269-291, 2011.

Y. Sakaguchi, I. Sekiya, K. Yagishita, S. Ichinose, K. Shinomiya and T. Muneta, "Suspended cells from trabecular bone by colagenase digestion becomes virtually identical to mesenchymal stem cells obtained from marrow aspirates," Blood, vol. 104, No. 9, pp. 2728-2735, 2004.

* cited by examiner

700 ↴

```
┌─────────────────────────────────────────────────┐
│ Force a liquid mixture through a cavitation     │
│ chamber at a pressure that separates pathogens  │
│ from particles in the mixture without           │──702
│ fragmenting at least 30 percent of the          │
│ pathogens                                       │
└─────────────────────────────────────────────────┘
```

```
┌─────────────────────────────────────────────────┐
│ Break down solids in a food substance into a    │──802
│ liquid mixture                                  │
└─────────────────────────────────────────────────┘
                        ↓
┌─────────────────────────────────────────────────┐
│ Filter particles from the liquid mixture        │──804
└─────────────────────────────────────────────────┘
                        ↓
┌─────────────────────────────────────────────────┐
│ Separate pathogens from particles in the        │
│ filtered, liquid mixture without fragmenting    │
│ at least 30 percent of the pathogens by         │──806
│ forcing the liquid mixture through a            │
│ cavitation chamber                              │
└─────────────────────────────────────────────────┘
```

*FIG. 8*

HYDRODYNAMIC CAVITATION

CROSS-REFERENCE TO RELATED APPLICATIONS

This application claims priority to and the benefit of U.S. Provisional Patent Application Ser. No. 62/811,499, filed Feb. 27, 2019 and titled "HYDRODYNAMIC CAVITATION." The foregoing is incorporated herein by this reference in its entirety.

BACKGROUND

The contamination of food and water sources by pathogens contributes to many illnesses throughout the world. Often pathogens can be found in food that has spoiled or through improper handling or storage. Samples of food or water may be tested for the presence pathogens, and in some cases, samples are broken down using a stomacher, which is a device that vigorously pounds the sample, employing compression and shearing forces to break the sample down into constituent parts and thereby create a homogenous mixture that can be used for testing. However, the mechanism of action of these devices can destroy the pathogen or otherwise make it difficult to identify the presence of pathogens following treatment.

SUMMARY

The principles disclose herein include a method for sample preparation, which may include obtaining a sample in the form of a liquid mixture and forcing the liquid mixture through a cavitation chamber at an optimal pressure for separating pathogens from particles in the mixture without fragmenting at least 30% of the pathogens.

In one aspect, forcing the liquid mixture through the cavitation chamber at an optimal pressure separates pathogens from particles in the mixture without fragmenting at least 50% of the pathogens. The optimal pressure can be between 5-20 PSI.

In one aspect, forcing the liquid mixture through the cavitation chamber at an optimal pressure separates pathogens from particles in the mixture without fragmenting at least 75% of the pathogens. The optimal pressure can be between 8-14 PSI.

In one aspect, the liquid mixture through the cavitation chamber at an optimal pressure separates pathogens from particles in the mixture without fragmenting at least 90% of the pathogens. The optimal pressure is between 8-14 PSI, preferably about 11 PSI. The method can additionally include breaking down solids in the liquid mixture with an enzyme prior to forcing the liquid mixture through the cavitation chamber. The method can also include filtering particles from the liquid mixture prior to forcing the liquid mixture through the cavitation chamber.

Embodiments of the present disclosure additionally include apparatuses for sample preparation. An exemplary apparatus includes a fluid circuit and a cavitation chamber incorporated into the fluid circuit. The cavitation chamber can include a channel, a first cross-sectional area of the channel and a second cross-sectional area of the channel that is smaller than the first cross-sectional area and oriented downstream from the first cross-sectional area with respect to fluid flow through the fluid circuit. The cavitation chamber can additionally include a third cross-sectional area of the channel that is larger than the second cross-sectional area and oriented downstream from the second cross-sectional area with respect to fluid flow through the fluid circuit. The apparatus can also include a pump in fluid communication with the cavitation chamber and a pressure sensor associated with the fluid circuit and positioned upstream of the cavitation chamber. The apparatus is configured to force a liquid mixture through the cavitation chamber at a pressure that separates pathogens from particles in the liquid mixture without fragmenting at least 30% of the pathogens.

In one aspect, the second cross-sectional area is formed by at least a first orifice defined in a cavitation plate disposed within the cavitation chamber.

In one aspect, the first orifice has a cross-sectional width that is between 0.5 mm and 1.5 mm. For example, the first orifice can have a cross-sectional width of about 0.8 mm and the first cross-sectional area of the channel has a cross-sectional width of about 1.2 mm.

In one aspect, the second cross-sectional area is formed by at least a first orifice and a second orifice defined in the cavitation plate, wherein the first orifice is spaced apart away from the second orifice at a distance, and wherein the first orifice and the second orifice allow a liquid to flow through the cavitation plate in parallel.

In one aspect, the third cross-sectional area is formed by an aperture defined by an expansion plate disposed downstream of the cavitation plate within the cavitation chamber. The first orifice can have a cross-sectional width less than 1.0 mm and the aperture can have a cross-sectional width greater than 1.0 mm. For example, the cross-sectional width of the first orifice can be about 0.8 mm and the cross-sectional width of the aperture can be at least 1.2 mm.

In one aspect, the apparatus includes a filter loop incorporated into the fluid circuit and a filter incorporated into the filter loop. The apparatus can also include a cavitation loop incorporated into the cavitation chamber and a directional control valve configured to selectively direct fluid into the cavitation loop and into the filter loop.

Methods for detecting a pathogen in a food substance are also disclosed. An exemplary method includes breaking down solids in the food substance to create a liquid mixture, fluidically coupling the liquid mixture to an apparatus for sample preparation disclosed herein; filtering the liquid mixture via the filter of the apparatus, and separating the pathogen from the filtered, liquid mixture without fragmenting at least 30% of the pathogens by forcing the liquid mixture through the cavitation chamber of the apparatus.

Any of the aspects of the principles detailed above may be combined with any of the other aspect detailed herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying drawings illustrate various embodiments of the present apparatus and are a part of the specification. The illustrated embodiments are merely examples of the present apparatus and do not limit the scope thereof.

FIG. 1 depicts an example of a fluid circuit in accordance with the present disclosure.

FIG. 2 depicts an example of preparing a liquid mixture in accordance with the present disclosure.

FIG. 3 depicts another example of a fluid circuit in accordance with the present disclosure.

FIG. 4 depicts an example of components in a cavitation chamber in accordance with the present disclosure.

FIG. 5A depicts an example of a front, inlet side of an orifice plate in accordance with the present disclosure.

FIG. 7 depicts an example of a method of sample preparation in accordance with the present disclosure.

FIG. 8 depicts another example of a method of sample preparation in accordance with the present disclosure.

Throughout the drawings, identical reference numbers designate similar, but not necessarily identical, elements.

DETAILED DESCRIPTION

Figure 1:
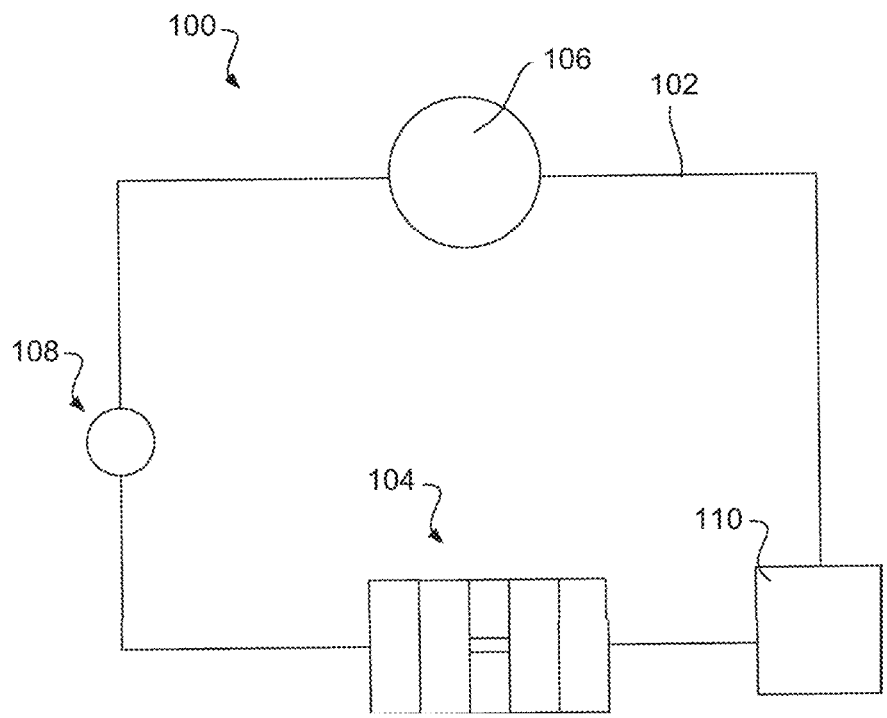

The principles disclosed herein provide a method for preparing a sample with a cavitation device. The prepared sample may be used in a subsequent process of testing the sample for the presence, concentration, and/or identity of pathogens. As used herein, the term "pathogen" includes the corpus of parasites and bacteria that can cause disease in humans or animals, typically via ingestion of contaminated food or water. The term "pathogen" should also be understood to include opportunistic pathogenic parasites and bacteria. In some instances, the term "pathogen" can include virions or viral capsids that cause disease in humans or other animals, typically via ingestion of contaminated food or water.

Additionally, or alternatively, the sample prepared with a cavitation device can be subjected to subsequent processes that may include, but is not limited to, testing the sample for other compounds or components, determining a characteristic of the sample, performing another process with the sample, or combinations thereof.

Cavitation is the formation of gas bubbles in a liquid caused by forces acting upon the liquid. It usually occurs when a liquid is subjected to rapid changes of pressure that cause the formation of the bubbles in regions of the liquid where the pressure is comparatively low. When subjected to higher pressure, the bubbles implode and generate intense shock waves. In many cases, cavitation is considered to be undesirable due to its destructive nature. For example, cavitation can erode gears, pipes, liners, and other components in hydraulic systems. Thus, hydraulic systems are usually constructed to prevent cavitation from occurring. However, cavitation has been used to destroy pathogens, and thereby sterilize fluids. For example, cavitation can be used to pasteurize eggs or to sterilize samples.

In some situations where the subsequent process includes testing for pathogens, the pathogens may be removed from the particles on which they are associated or attached during cavitation. For example, pathogens may be located in a liquid (e.g., water or other potable liquid) or on a solid medium (e.g., meat, vegetables, fruits, or other food). In these cases, the pathogens can be disassociated from the given substrate or medium as a result of cavitation such that the pathogen can be identified and/or quantified. Treatment of the sample via cavitation may also beneficially break up bacterial biofilms (e.g., monoclonal or polyclonal biofilms) within the sample and thereby more easily allow for the identification and/or quantification of bacterial pathogens within the sample. The principles disclosed herein include a process for removing the pathogens from particles in a liquid mixture without fragmenting or otherwise destroying at least a subset of the pathogens during processing.

The term "fragmenting," or similar, when used herein in reference to pathogens, is used to connote the shearing of a portion of the pathogen (e.g., the removal of extracellular portions of a parasite or bacterium such proteins, lipids, polysaccharides, or a combination thereof that are associated with the pathogen) or a physical disruption of the structural integrity of the pathogen that causes the pathogen to no longer be viable and/or pathogenic. It should be appreciated that the term "fragmenting," or similar, includes separating the pathogen into multiple pieces or fragments that cannot be detected using standard molecular biological and/or diagnostic techniques. Portions of the pathogen may be forcibly removed or shorn (e.g., when forcibly removed from association with particles in a sample by cavitation forces) without "fragmenting" the pathogen. For example, a cavitation force that removes a pathogen from a particle may cause adhesins or portions of adhesins (e.g., pili, fimbriae, etc.) to shear or break away from the pathogen without "fragmenting" or destroying the viability or detectability of the pathogen. Similarly, a cavitation force may fragment a biofilm or other polymicrobial association without destroying at least some of the metabolically active pathogens within the biofilm and thereby allow for their identification and/or quantification. Accordingly, as used herein, the filtering or separation of pathogens from "particles" during cavitation can include physical disassociation of the pathogen from the solid or from contaminants within the liquid but also includes the breaking apart of biofilms or other polymicrobial association to allow for the identification and/or quantification of pathogenic bacteria associated with the sample. It should be appreciated that while the disclosure may be focused on pathogen identification and/or quantification, the methods disclosed herein can additionally be used to identify non-pathogenic prokaryotic or eukaryotic contaminants.

The filtering or separation of the pathogens from these particles allows for testing to be performed that can identify whether the food, water, or other types of samples are contaminated. For example, a military encampment may be located far away from testing labs but may nevertheless be able to determine whether the food they packed with them or the natural food and water sources around them are contaminated. These food/water sources may be prepared for testing. In some cases, food, like meat, may be prepared in a liquid mixture by breaking down the fibers of the meat. Enzymes or other types of materials may be added to the meat that can break down the meat's fibers. Different types of food or water may be processed for different times and/or with different chemical or enzymatic steps prior to or coincident with its preparation into a liquid mixture, depending on the type of food or water type. An initial enzymatic (or other pre-processing) step can beneficially prepare the sample for cavitation without disrupting the metabolic activity (or in the case of viruses, the infectability) of pathogens associated with the sample while also preparing the sample in the form of a liquid mixture amenable to processing via one or more cavitation methods disclosed herein.

With the sample as a liquid mixture, the liquid mixture can be further filtered, if desired, to remove certain types of particles. Particles that may be desirable to remove are large particles, fat particles, other types of particles that tend to coalesce back to each other, other types of particles, or combinations thereof. Fine mesh colanders, size exclusion filters, charged filters, or other means of filtration or separating contents can be used as known in the art.

When the liquid mixture is filtered or pretreated to a desirable point, the liquid mixture can be passed through a cavitation chamber. The cavitation chamber may include the characteristics that cause bubbles to form in the liquid mixture in a lower pressure area and then to cause the bubbles to collapse in a higher-pressure area. The collapse of the bubbles may release an amount of energy that is sufficient to separate at least some of the pathogens off of the particles in the liquid mixture-without fragmenting the pathogens-so that the pathogens, if present, can be isolated. The particles from which the pathogens are intended to be removed from can be filtered out of the liquid mixture. The remaining portion of the sample can be tested for the presence of the pathogens. If the test results are negative, then a determination can be made that the original sample was (likely) not contaminated with pathogens. On the other hand, if pathogens are detected in the remaining portion of the sample, then a determination can be made that the original sample is contaminated with pathogens. In these circumstances, consumption of food or water from the contaminated sample's source can be avoided, thereby reducing potential morbidity from consumption of contaminated food/liquid.

Conventional use of hydrodynamic cavitation includes sterilizing samples by fragmenting any pathogen (or non-pathogen) contaminant. However, it was observed that under certain controlled parameters, cavitation can be used to separate or otherwise release pathogens from the sample without fragmenting the pathogens, beneficially allowing for the identification and/or quantification of pathogens within the sample. One of these controlled parameters includes the input pressure through which the liquid mixture is supplied into the cavitation chamber. The appropriate input pressure may depend on the type and the physical characteristics of the cavitation chamber. For example, the pressure drop in different cavitation chambers may affect the appropriate input pressure of the liquid mixture. Further, the diameters of the channel upstream and downstream of the higher-pressure regions in the cavitation chamber may affect the appropriate input pressure. Additionally, the appropriate input pressure may be affected by the presence of an orifice plate or whether the cavitation chamber has a different mechanism for increasing the pressure.

In cases where the input pressure is too high, pathogens are more likely to be destroyed during the cavitation process, which can result in a false negative result from subsequent testing for determining whether the original sample included pathogens. On the other hand, input pressure that is too low may not result in cavitation or in cavitation forces that are insufficient for disassociating the pathogens from particles in the liquid mixture to allow for their identification and/or quantification, similarly resulting in a false negative.

Under the experiments performed, it was found that in a certain hydrodynamic cavitation chamber, described in more detail below, an optimal input pressure range was between 8 PSI to 14 PSI. However, pressures up to 20 PSI and even higher were still observed as allowing pathogen detection in testing that occurred after cavitation. In the foregoing example, the particular cavitation chamber utilized included a 1.2 mm channel in the upstream and downstream portions of the chamber with an orifice plate between the upstream and downstream portions. The orifice plate had a single aperture allowing the liquid mixture to pass through the orifice plate. The aperture was 0.8 mm on the inlet side and 1.2 mm on the outlet side.

However, in other embodiments, it is foreseen that multiple apertures can be incorporated into the orifice plate allowing the liquid mixture to pass through a plurality of apertures in parallel. As an example, the orifice plate could incorporate between two and ten apertures or any other desirable number of apertures. In some embodiments, the increased number of apertures allows a larger volume of sample to be processed while maintaining a similar cumulative pressure into and/or through the orifice plate.

Now referring to the figures, FIG. 1 depicts an example of a fluid circuit 100 in accordance with the principle described herein. In this example, the fluid circuit 100 includes a flow path 102 that can direct the flow of a liquid mixture. The flow path 102 connects to the cavitation device 104 that includes a cavitation chamber, a pump 106, a pressure sensor 108, and the sample reservoir 110. The sample may be circulated in and out of the cavitation device via the flow path using the pump 106 (e.g., a peristaltic pump). Input pressure to the cavitation device 104 may be measured, for example, by the pressure sensor 108.

The sample reservoir 110 may be include a liquid mixture that is prepared for passing and/or circulation through the cavitation device 104. In some cases, the liquid mixture within the sample reservoir 110 includes meat or other food components that have been mechanically and/or chemically broken down and which may have been filtered or pretreated. Water or other potable fluid may also constitute the liquid mixture placed in the sample reservoir 110. In some cases, water (or other potable fluid) samples may optionally undergo processing between the Lime that the water is extracted from its natural source and the Lime that the water is circulated through the cavitation device.

In some cases, the flow path 102 is defined by a flexible tube that can transport a fluid. In an embodiment where the flow path 102 is defined with a flexible tube, the liquid mixture may be moved by the forces exerted on the liquid mixture by the pump 106 (e.g., a peristaltic pump or any other appropriate type of pump). In some embodiments, the pump 106 is a positive displacement peristaltic pump. A portion of the flexible tube defining the flow path may be fitted inside the peristaltic pump's casing. The pump may include a rotor that has several rollers or similar devices attached to the external circumference of the rotor. The rollers may be positioned on the rotor such that the rollers are in physical contact with the portion of the flexible tube in the pump's casing and move along the length of this section of the flexible tube as the rotor is rotated. The rollers are operable to compress the flexible tube such that the part of the flexible tube under compression is pinched closed or otherwise narrowed to a smaller diameter, and as the rotor turns, the rollers move along the flow path, causing the closed or narrowed portion to advance along the flow path. This, in turn, forces the liquid mixture downstream of the rollers to be forced along the flow path, and as the rollers advance, the previously closed or narrowed tubing expands, pulling the liquid mixture upstream of the rollers along the flow path. Thus, by activating the rotor of the peristaltic pump, the liquid mixture may be pumped out of the sample reservoir towards to the cavitation device 104.

The pressure sensor 108 may be positioned downstream of the pump 106, but upstream of the cavitation device 104. In this example, the pressure in the flow path 102 between the pump 106 and cavitation device 104 may be indicative of the input pressure into the cavitation device 104. Any appropriate type of pressure sensor may be used to measure the pressure in this section of the flow path 102. For example, a non-exhaustive list of sensor types may include, but is not limited to, in-line sensors, stain gauges, piezoresistive sensors, capacitive sensors, electromagnetic sensors, piezoelectric sensors, optical sensors, potentiometric sensors, resonant sensors, thermal sensors, other types of sensors used to measure the pressure of a liquid mixture in the flow path, or combinations thereof.

The cavitation device 104 induces a cavitation effect on the liquid mixture as the flow travels through the cavitation device 104. In some embodiments, the cavitation device 104 includes a chamber that has a first expansion region with a comparatively low pressure and that is disposed upstream of a high-pressure area in the cavitation device 104. A second expansion region can be disposed downstream of the high-pressure area. Bubbles of gas form in the lower pressure area as the liquid mixture travels through the high-pressure area into the second expansion region where the pressure is relatively lower than in the high-pressure area. As the liquid mixture travels farther away from the region exhibiting the pressure drop, the pressure in the flow path gradually increases. As the pressure increases, the bubbles implode generating shock waves through the liquid mixture. With an optimal input pressure, these shock waves are powerful enough to cause at least some pathogens within the sample, if any are present, to be released from the other particles in the sample without fragmenting the pathogens.

In some embodiments, the sample may be recirculated through the cavitation device 104 multiple times so that the sample can be subjected to the cavitation forces multiple times, as desired. For example, input pressures at the lower end of the optimal pressure range may reduce the likelihood of pathogen fragmentation or be associated with a higher pathogen "survival" rate (i.e., the % or proportion of non-fragmented pathogens following processing through the cavitation device) but samples processed at this lower optimal pressure may benefit from multiple passes (e.g., three or more) through the cavitation device to ensure release of the pathogens from the particles in the sample. On the other hand, input pressures at the upper end of the optimal pressure range may increase the likelihood of pathogen fragmentation or be associated with a lower pathogen survival rate but samples processed at this higher optimal pressure may benefit from fewer (e.g., one or two) passes through the cavitation device.

In some embodiments, the pathogen survival rate following singular or serial processing through the cavitation device is greater than or equal to 30%. Higher survival rates are additionally envisioned and preferred, such as at least 50%. In some embodiments, the sample is processed such that the survival rate of the pathogens is at least 75%, meaning at least 75% of the pathogens remain intact and are identifiable and/or quantifiable. In some embodiments, the sample is processed such that the survival rate of the pathogens is at least 90%.

It should be appreciated that any appropriate type of cavitation device may be used to induce the cavitation effect on the liquid mixture. For example, the cavitation device may be an orifice cavitation device, a venturi cavitation device, an ultrasonic cavitation device, an impeller cavitation device, another type of cavitation device, or combinations thereof.

In some cases, communication between the pressure sensor 108 and the pump 106 allow for the pressure to be maintained within an appropriate range that causes pathogen dissociation without fragmenting the pathogens. In some cases, a signal may be sent to the pump 106 from the sensor 108 that causes the pump 106 to increase or decrease the input pressure. In some cases, the input pressure can be controlled by, for example, controlling the rotary speed of the rotor within a peristaltic pump. In other examples, the pressure measurements may indicate to a technician that an input pressure adjustment is desirable, and the technician can deliver a manual input to cause the pump to alter the input pressure.

Referring now to FIG. 2, depicted is an example method of sample preparation that includes pretreating a meat sample prior to running the meat sample through a cavitation device (not shown). In this example, the meat 200 is placed in a liquid solution 202 on a heating element 204. An enzyme 206 is added to the liquid solution 202 to break down the meat. The liquid solution 202 may be stirred or agitated.

Meat may be more difficult than other food types to homogenize into a liquid mixture due to its relatively abundant and strong proteins and connective tissues, such as collagen and myofibrillar proteins. These types of proteins and connective tissues could lead to clogging of the cavitation device. In some cases, a pretreatment step may be used to "soften" these proteins and other meat constituents (e.g., partial proteolysis or degradation of cellular junctions) for passage through the cavitation chamber. In some cases, a proteolytic enzyme, like Papain found commonly in papaya fruit and meat tenderizer, may be used to break down these tissues. Papain is an aggressive enzyme that facilitates the degradation of both myofibrillar proteins and collagen. While this example identifies Papain as an enzyme to break down the meat, other tenderizers and/or enzymes may be used.

In one example, beef was mixed with a solution containing 90 mL of deionized water and 6.6 grams of Papain to tenderize the sample. These samples were placed in a water bath at 70° C. for one and a half hours with constant stirring to allow for optimal enzymatic activity of Papain. This pretreatment resulted in the creation of a mixture of liquefied beef, fat, and collagen. Samples were prefiltered by passing them through a coffee filter with 0.8 mm holes cut throughout it at a roughly 30% fill density to collect any solids. The filter recovered from this process typically contained less than 10% of the initial solid sample. The liquid beef mixture filtrate was then passed through the hydrodynamic cavitation device for seven and a half minutes at a predetermined input pressure.

In another example, ground beef samples were purchased from a local grocery store and prepared for use in the experiments. Ground beef samples containing 85% lean content 15% fat content were partitioned into 50 g samples, flattened into thin sheets to aid with thawing, and stored at −20° C. for further use. Samples meant for testing were rapidly thawed in accordance to methods described by the U.S. FDA's Bacteriological Analytical Manual. After thawing, inoculation was conducted by immersing 10 grams of ground beef in 10 mL of 1× PBS. 100 μL of the desired pathogen was then added to each sample followed by incubation for 90 minutes to allow pathogens to grow on the meat.

Figure 3:
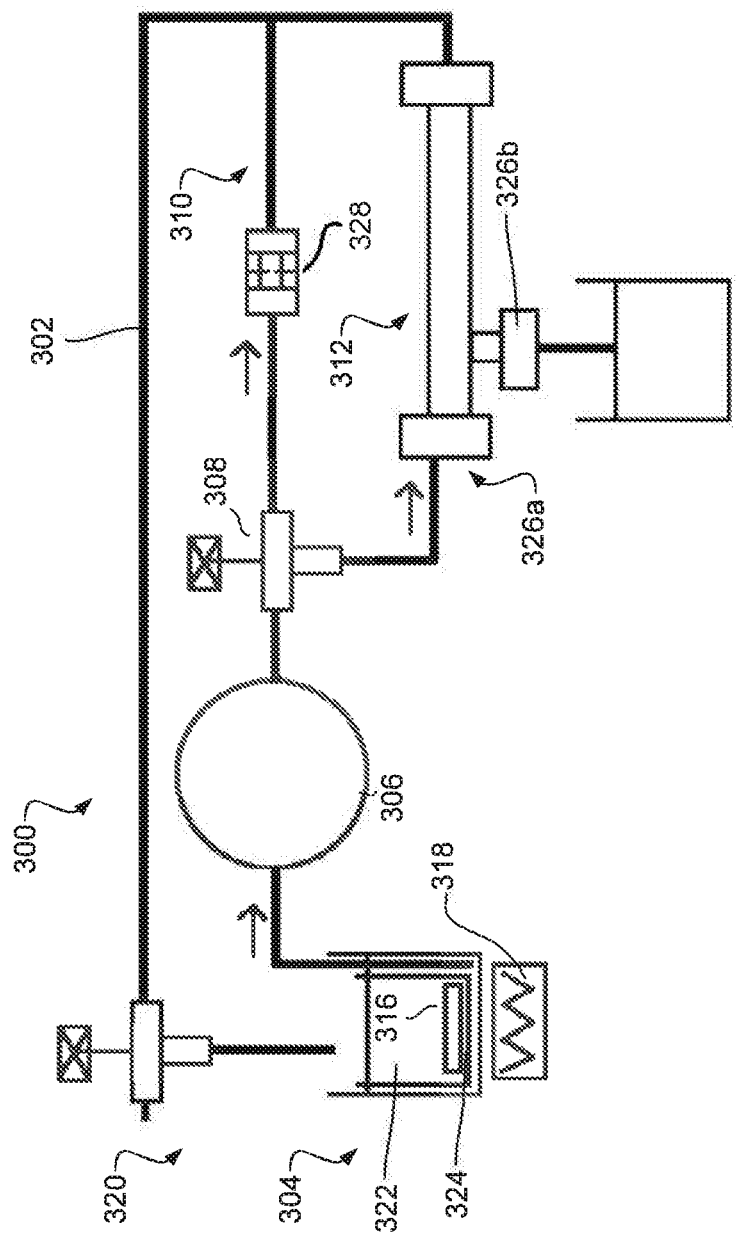

Referring now to FIG. 3, illustrated is another example of an apparatus 300 that can be used to prepare a sample. In the depicted example, the apparatus 300 may cavitate the liquid mixture to remove the pathogens from the particles in the liquid mixture without fragmenting the pathogens. In this example, the apparatus 300 includes a flow path 302, a sample reservoir 304, a pump 306, a directional control valve 308, a cavitation loop 310, and a filtering loop 312.

With continued reference to FIG. 3, the sample reservoir 304 includes a first filter 314 and a stir rod 316. The first filter 314 can be used to remove debris of non-interest from the flow path 302. In some examples, coffee filters, or other size exclusion filters, may be used as the first filter 314. The stir rod 316 or another type of agitator may keep the constituents of the liquid mixture from coalescing. For example, fat and other types of lipids may tend to coalesce. Additionally, a heater 318 may be used to keep the liquid mixture at a desirable temperature for flowing through the flow path 302.

An outlet 320 may deliver the liquid mixture into the sample reservoir on a pre-filtered region 322 of the sample reservoir 304. In some cases, the outlet 320 delivers liquid mixture that has been through at least a portion of the flow path 302 or the outlet 320 may deliver fresh liquid mixture that has not yet been processed by the apparatus 300.

The flow path 302 may connect the pump 306 to a post-filtered side 324 of the sample reservoir 304. The pump 306 may create a pressure differential that draws liquid mixture from the sample reservoir 304 into the flow path 302. Any appropriate type of pump may be used to move the liquid mixture along the flow path 302. For example, a peristaltic pump (Item #EW-07553-70). Masterflex LIS Easy-Load II Pump Heads (Item #HV-77200-60), and Masterflex C-Flex tubing LIS 17 (Item #HV-06424-17) may be suitable and may be purchased from Cole-Parmer (Vernon Hills, IL).

The directional control valve 308 may selectively direct the liquid mixture through the filtering loop 312 or the cavitation loop 310. In some cases, the directional control valve 308 is initially set to direct the liquid mixture into the filtering loop 312 where a second filter 326 is used to remove additional types of debris in the liquid mixture. In some cases, the second filter 326 may include a tangential flow filter **326*a* and a secondary filter 328*b***.

Tangential flow filtration may be different from dead-end filtration in which the feed is passed through a filter membrane. The tangential flow filter allows the liquid mixture to travel tangentially across the surface of the filter membrane rather than through the filter membrane. The tangential flow filter can be advantageous as the build-up on the filter's face is spread over a greater cross-sectional area during the filtration process, increasing the length of time that a filter unit can be operational.

A discharge mechanism may be incorporated into the filtering loop where the debris of other types of filtrates can be removed from the filtering loop 312. In some cases, the liquid mixture may be circulated through the filtering loop 312 back into the sample reservoir 304 multiple times before the directional control valve 308 is set to direct the liquid mixture into the cavitation loop 310.

The cavitation loop 310 may include a cavitation chamber 328 where the liquid mixture is subjected to the cavitation forces that separate the pathogens, if any, in the sample from the particles in the liquid mixture. The apparatus 300 may be used to circulate the liquid mixture through the cavitation loop 310 multiple times before the liquid mixture is purified to a desired level for testing for the presence, concentration, or identity of pathogens in the sample or for another subsequent process.

To prevent the pathogens from being fragmented, the input pressure into the cavitation loop should not be too high. Further, if the input pressure is too low, the cavitation effect may not occur or be strong enough to separate the pathogens from particles in the liquid mixture. In some situations, the optimal input pressures into the cavitation loop and into the filtering loop may not be the same. In these types of situations, the pump may provide a different input pressure when the liquid mixture is directed through the filtering loop than when the liquid mixture is directed through the cavitation loop.

With reference now to FIG. 4, illustrated is an exploded view of an exemplary cavitation chamber 400. As shown, the cavitation chamber 400 includes fittings 401 and expansion discs 402 on either side of an orifice plate 404. A face 500 of the orifice plate 404 is depicted in FIGS. 5A and 5B. As shown, the orifice plate 404 includes single aperture having an inlet 502, depicted in FIG. 5A, that is larger than the outlet 504, depicted in FIG. 5B. As the liquid mixture is forced through the cavitation chamber, the liquid mixture travels through the channel of the first, upstream set of fittings 401 and expansion disc 402 (left/upstream side of plate 404, as shown). A pressure build-up occurs due to the decreased flow of the liquid mixture as the liquid mixture travels through the apertures of the orifice plate 404. After passing through the orifice plate 404, the liquid mixture experiences a low pressure as the diameter of the channel in the expansion disc 402 downstream of the orifice plate expands. In this expanded diameter, the cavitation bubbles are created. The cavitation bubbles can then be disrupted, dislodging the pathogens, if present, and a portion of the cavitated mixture sequestered for testing.

The process of preparing a sample may involve pretreatment of food samples and cavitation of food samples as described above. A subsequent process may be to test the sample of pathogens. This subsequent process may include electrochemical detection of the pathogen using, for example, a system that immunomagnetically captures pathogens from food/water samples, removes non-target particles from the system, amplifies the electrochemical signal via use of electrochemical marker coated secondary beads, elutes electrochemical marker from the secondary beads, and electrochemically detects the marker. In some cases, the pathogens can be bound to metal or other material in combination with being bound to the electrochemical marker or in lieu of the electrochemical marker.

To capture the pathogens in the third step, anti-pathogen antibody coated magnetic primary beads capture pathogens in the sample. Removal of non-target particles can be facilitated through the magnetic concentration of the primary beads associated with the target particles, flushing the remaining sample and washing the beads, as known in the art. The pathogens that are captured in this step may then be attached to a second set of beads via conjugated anti-pathogen antibodies. The secondary beads can include single or multiple electrochemical or other types of tags. Such a procedure enables the system to only contain primary-magnetic-bead-pathogen-secondary-bead complexes, from which the electrochemical marker can be detached from the secondary bead using an elution buffer and transferred to an electrochemical detector for quantification and/or identifying the presence of pathogen (e.g., by two square wave voltammetry scans that create a signal indicative of the presence/absence of pathogen). The secondary bead can also serve as a marker itself.

For example, electrochemical measurements may be made using a Palmsens EmStat3+ potentiostat (Order code: ES3P-USB) with accompanying Pstrace 4.8 control software (Houten, The Netherlands). Screen printed carbon electrodes (Catalog #DRP-96X1 10) that can be purchased from Dropsens in a 96-well plate format (Llanera, Asturias Spain) may also be used. The electrochemical cells may include a carbon counter electrode, a 3 mm diameter carbon working electrode, and a silver pseudo-reference electrode. A custom printed magnetic separation rack (or similar) may be used to concentrate the magnetic beads into a pellet. A Labnet Mini LabRoller Dual Format Rotator (or similar) may be used to resuspend the solutions (Edison, NJ). An Autolab Faraday cage available from Metrohm Autolab B.V. (Utrecht, Netherlands) (or similar) can be used to prevent electrical interference from surrounding electronics during electrochemical measurements.

Figure 6:
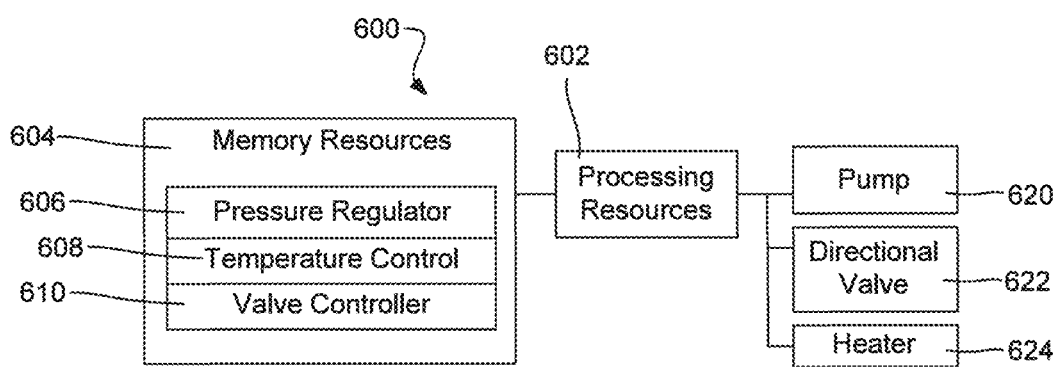
FIG. 6 depicts an example of a portion of a cavitation control system in accordance with the present disclosure.

FIG. 6 illustrates a schematic of an exemplary cavitation control system 600 in accordance with the present disclosure. The cavitation control system 600 can include a combination of hardware and computer executable instructions for executing the functions of the cavitation control system 600. As shown, the cavitation control system 600 includes processing resources 602 that are in communication with memory resources 604. Processing resources 602 include at least one hardware or software processor and other resources used to process the computer executable instructions. The memory resources 604 represent generally any memory capable of storing data such as computer executable instructions or data structures used by the cavitation control system 600 and are preferably embodied as or within hardware storage devices. The computer executable instructions and data structures shown stored in the memory resources 604 include instructions for operating and/or controlling operation of a pressure regulator 606, a temperature control 608, and a valve controller 610.

The processing resources 602 may be in communication with a pump 620, a directional valve 622, and a heater 624. Each of the pump 620, directional valve 622, heater 624, memory resources 604, and processing resource 602 may be incorporated into a single device. In other examples, at least some of these components may be incorporated into two or more devices. In yet other examples, at least some of the computer executable instructions stored in the memory resources 604 are located in a device with these components. But, in other examples, at least some of the memory may be accessible from a remote location, such as networked or cloud-based sources.

In examples where at least some of the processing resources 602, memory resources 604, and the other components are not embodied in a single device, the processing resources 602, memory resources 604, and/or components of system may communicate over any appropriate network and/or protocol through a communications interface. In some examples, the communications interface includes a transceiver for wired and/or wireless communications. For example, these devices may be capable of communicating using the ZigBee protocol, Z-Wave protocol, Bluetooth protocol, Wi-Fi protocol, Global System for Mobile Communications (GSM) standard, another standard or combinations thereof. In other examples, the user can directly input some information into the trigger system 900 through a digital input/output mechanism, a mechanical input/output mechanism, another type of mechanism or combinations thereof.

The memory resources 604 include a computer readable storage medium that contains computer executable instructions configured to cause tasks to be executed by the processing resources 602. The computer readable storage medium may be a hardware and/or non-transitory storage medium. The computer readable storage medium may be any appropriate storage medium that is not a transmission storage medium. A non-exhaustive list of computer readable storage media includes non-volatile memory, volatile memory, random access memory, write only memory, flash memory, electrically erasable program read only memory, magnetic based memory, other types of memory or combinations thereof.

The pressure regulator 606 includes computer executable instructions that, when executed, cause the processing resources 602 to control the input pressure into the cavitation chamber. In some examples, a pressure sensor measures the pressure of the liquid mixture between the pump 620 and cavitation chamber. In response to measuring that the pressure is too high, the pressure regulator 606 may send a signal to the pump 620 to decrease the pressure. In some cases, the pressure may be lowered by rotating a rotor of a peristaltic pump slower. In response to measuring that the pressure is too low, the pressure regulator 606 may send a signal to the pump to increase the pressure. In those examples with a peristaltic pump, the pressure may be increased by increasing the rotary speed of the pump's rotor.

The temperature control 608 includes computer executable instructions that, when executed, cause the processing resources 602 to control the temperature of the heater 624. The heater 624 may be located in the sample reservoir and can be used to breakdown substances in the liquid mixture, to prevent fats or other lipid-based substances from coalescing, and/or to control a temperature of the liquid mixture throughout the filtering or cavitation loops that may optimize the filtering or the cavitation.

The valve controller 610 includes computer executable instructions that, when executed, cause the processing resources 602 to control the directional valve. When it is desirable to direct the liquid mixture to the filtering loop, the valve controller 610 may cause the physical components of the directional valve to be oriented so that the liquid mixture is directed into the filtering loop. When it is desirable to direct the liquid mixture to the cavitation loop, the valve controller 610 may cause the physical components of the directional valve to be oriented so that the liquid mixture is directed into the cavitation loop.

Further, the memory resources 604 may be part of an installation package. In response to installing the installation package, the computer executable instructions of the memory resources 604 may be downloaded from the installation package's source, such as a portable medium, a server, a remote network location, another location or combinations thereof. Portable memory media that are compatible with the principles described herein include DVDs, CDs, flash memory, portable disks, magnetic disks, optical disks, other forms of portable memory or combinations thereof. In other examples, the program instructions are already installed. Here, the memory resources 604 can include integrated memory such as a hard drive, a solid-state hard drive, or the like.

In some examples, the processing resources 602 and the memory resources 604 are located within a mobile device, an external device, networked device, a remote device, another type of device, or combinations thereof. The memory resources 604 may be part of any of these device's main memory, caches, registers, non-volatile memory, or elsewhere in their memory hierarchy. In some cases, the memory resources 604 may be in communication with the processing resources 602 over a network.

FIG. 7 illustrates an exemplary method flow for a method 700 of sample preparation in accordance with the present disclosure. In this example, the method 700 includes forcing a liquid mixture through a cavitation chamber at a pressure that separates pathogens from particles in the mixture without fragmenting at least 30% of the pathogens (act 702).

At act 702, the liquid mixture is forced through a cavitation chamber with a pressure that separates pathogens from particles in the mixture without fragmenting at least 30% of the pathogens (e.g., 70% of the pathogens are identifiable and/or quantifiable). In some cases, the pressure results in the pathogens being separated with at least 50% of the pathogens remaining intact. In some cases, the pressure results in the pathogens being separated with at least 75% the pathogens remaining intact. In yet additional cases, the pressure results in the pathogens being separated with at least 90% the pathogens remaining intact. In some embodiments, the pressure results in the pathogens being separated with approximately all the pathogens remaining intact.

In some cases, the pressure is between 5 PSI and 20 PSI. In other examples, the pressure is between 8 PSI and 14 PSI. In another example, the pressure is between 10 PSI and 12 PSI. However, while these pressures have been determined to achieve the result of separating the pathogens while keeping a significant portion or even a majority of the pathogens from fragmenting, the input pressure may be different for cavitation devices that have different channel diameters, different channel lengths, different sized orifices, orifice plate's with different thicknesses, different high pressure to low pressure ratios, different low pressure to high pressure ratios, other different cavitation chamber parameters, or combinations thereof.

FIG. 8 illustrates an exemplary flow diagram of a method 800 of sample preparation in a sample in accordance with the present disclosure. In this example, the method 800 includes breaking down solids in a food substance into a liquid mixture (act 802), filtering particles from the liquid mixture (act 804), and separating pathogens from particles in the filtered, liquid mixture without fragmenting at least 30% of the pathogens by forcing the liquid mixture through a cavitation chamber (act 806).

At act 802, solids in a food substance are broken down into a liquid mixture. In some cases, an enzyme or another substance is added to the food particles to break the food substances down into a liquid mixture. In some cases that involve samples with meat, the enzyme Papain may be added to the solution with the meat. To break down the food substance, the food substance may be stirred in a liquid and heat may be applied to aid in the break down process.

At act 804, particles in the liquid mixture may be filtered out of the liquid mixture. In some examples, the filters depicted in FIG. 3 may be used, such as dead-end filters, tangential flow filters, coffee filters, other types of filters, or combinations thereof. The liquid mixture may go through multiple rounds through one or more filters to remove the particles from the liquid mixture.

At act 806, the pathogens in the liquid mixture, if any pathogens exist, are separated from the mixture's particles. The pathogens are separated in a manner where at least 30% of the pathogens survive the separation process by forcing the pathogens through a cavitation chamber. The input pressure at which the liquid mixture is forced through the cavitation is high enough that the pathogens are separated from the particles, but low enough that the pathogens are not destroyed as they pass through the cavitation chamber.

Figure 12A:
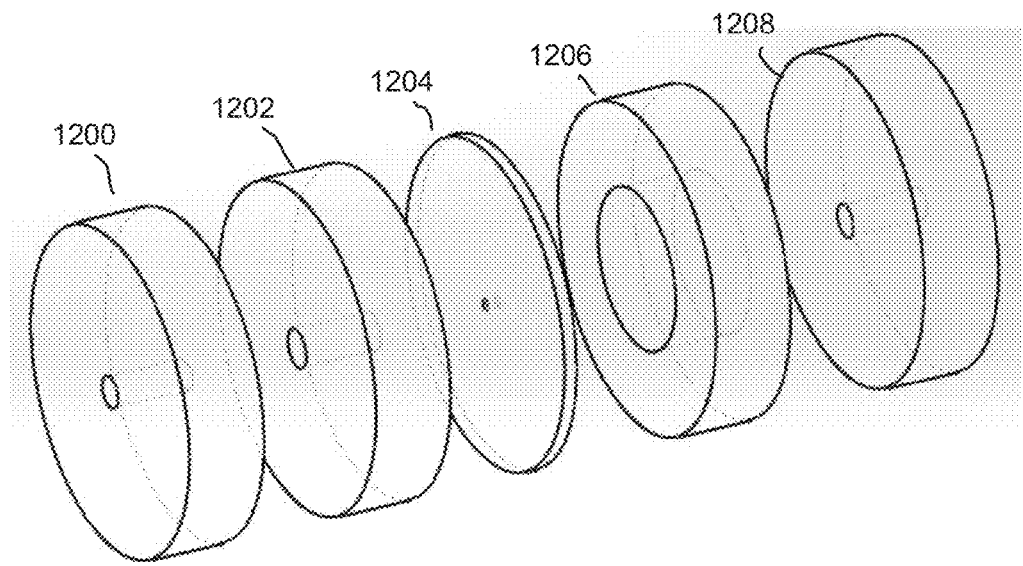
FIG. 12A depicts an example of components in a cavitation chamber in accordance with the present disclosure.
Figure 12B:
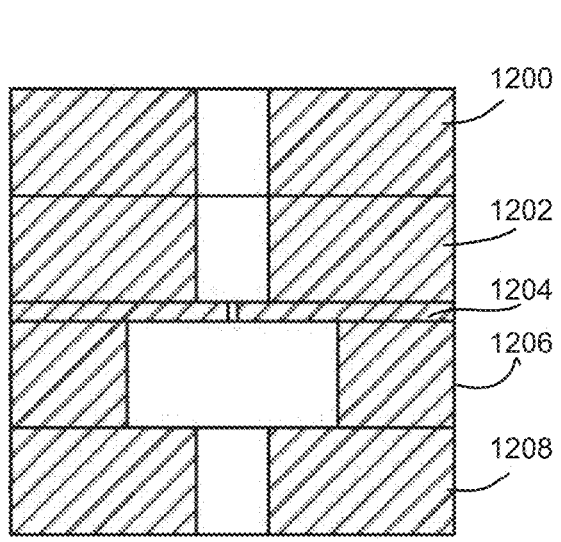
FIG. 12B illustrates a cross sectional view of the assembled components of FIG. 12A in accordance with the present disclosure.

With reference now to FIG. 12A, illustrated is an exploded view of an exemplary cavitation chamber. As shown, the cavitation chamber includes a plurality of discs 1200, 1202, 1204, 1206, 1208. While the number of discs may vary from embodiment to embodiment, the illustrated chamber includes five total discs with two discs 1200, 1202 flanking the upstream side of an orifice plate 1204 and two additional discs 1206, 1208 flanking the downstream side of the orifice plate 1204. FIG. 12B illustrates a cross section of the cavitation chamber of FIG. 12A that perhaps better illustrates the different diameter apertures formed in each of the discs 1200, 1202, 1204, 1206, 1208 that comprise the illustrated cavitation chamber. As illustrated, the upstream discs 1200, 1202 each define apertures that have the same cross sectional width. The orifice plate 1204 includes an aperture that has a smaller cross sectional width than those discs both upstream and downstream from it. On the downstream side, the first disc 1206 flanking the orifice plate 1204 defines an aperture that has a cross sectional diameter that is greater than that formed by the orifice plate 1204 and also greater than that formed by the upstream discs 1200, 1202. The final disc 1208 illustrated defines an aperture with a smaller cross sectional width than the disc 1206 immediately upstream of it but which is still larger than the cross sectional width of the aperture defined by the orifice plate 1204.

Figure 2:
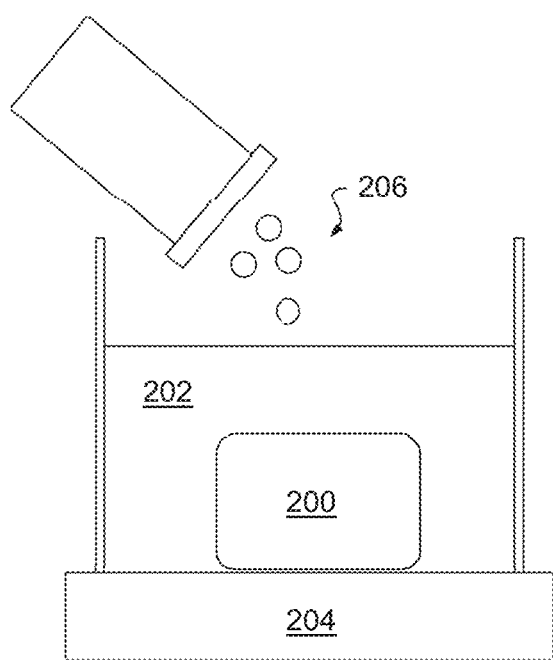
Figure 12C:
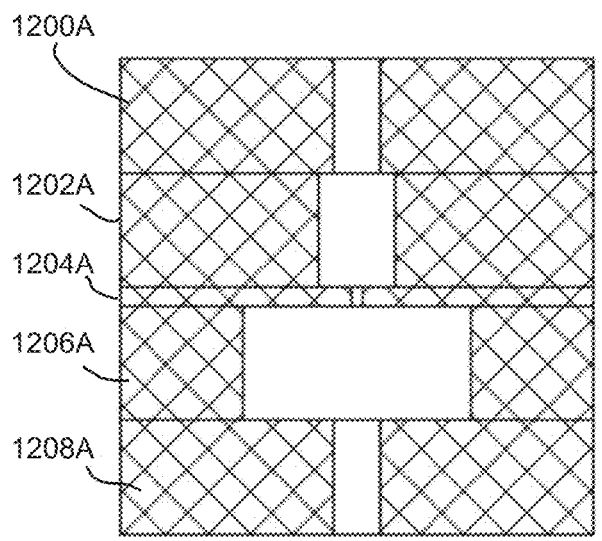
FIG. 12C illustrates a cross sectional view of another exemplary cavitation chamber in accordance with the present disclosure.

As a non-limiting example, the cross-sectional width of apertures formed into 25 mm wide discs can be (in an upstream to downstream orientation, as depicted in FIG. 2B) 4 mm, 4 mm, 0.8 mm, 12 mm, 4 mm. Other dimensions are considered within the scope of this disclosure, including those shown in FIG. 12C. The cross-sectional width of apertures formed into 25 mm wide discs illustrated in FIG. 12C can be (in an upstream to downstream orientation, as depicted in FIG. 12C) M3×0.5 tapped hole of 2.50 mm (disc 1200A), 4.04 mm through hole (disc 1200B), 0.635 mm through hole (orifice plate 1204A), 12 mm through hole (disc 1206A), and a M3×0.5 tapped hole of 2.50 mm (disc 1208A).

Figure 13:
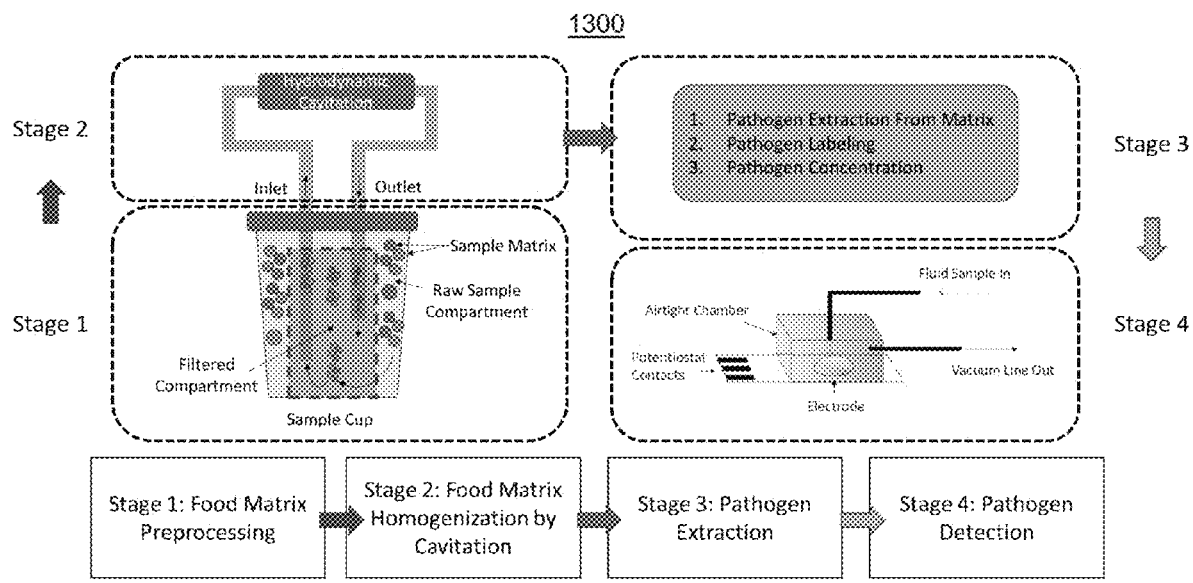
FIG. 13 is a model of an exemplary continuous flow system incorporating hydrodynamic cavitation devices and systems in accordance with the present disclosure.
Figure 14:
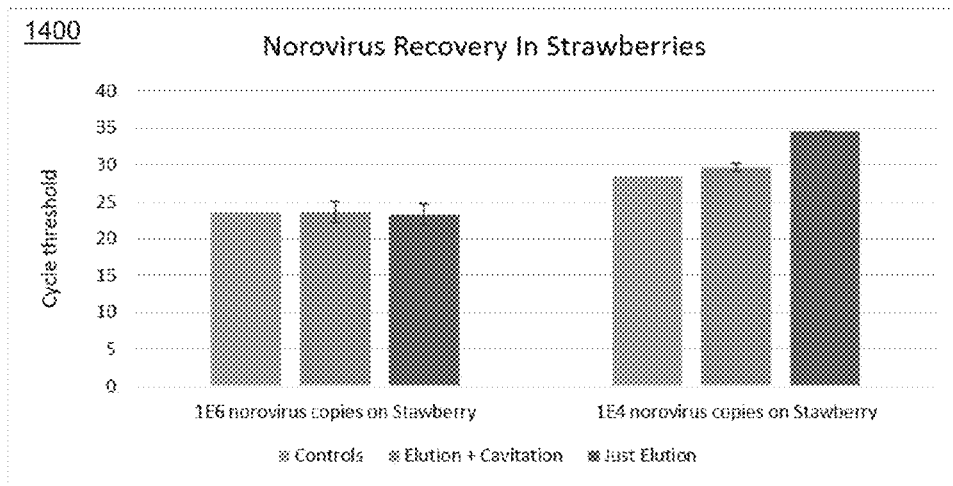
FIG. 14 is a graph illustrating results of detecting a virus in a sample of strawberries using cavitation methods and systems in accordance with the present disclosure.

Referring now to FIG. 13, a continuous flow system is also envisioned within the scope of this disclosure. For example, an integrated pathogen analysis system 1300 can enable a single user to input a specified food or water sample for continuous-process sample prep, pathogen extraction, pathogen detection, and answer output. The diagrammatically illustrated design of FIG. 13 minimizes user interaction and input with the instrument. A sample processing cup containing a filtration unit and mixing paddle can be used with a vortex system or similar for generating pulses/pressure waves. Parameters, including vortex/pulse intensity, duration, and flow rate, can be tuned to optimize the processing of unique food matrices. For example, samples containing berries would require less intense vortexing as compared with a ground beef sample. Established protocols are selected by the user based on the sample type. Testing of the sample cup shows that the 10 g of ground beef can be placed directly into the cup and then loaded onto the vortex unit. The preprocessed sample can then be pumped directly into the cavitation device for homogenization and then on to pathogen extraction and detection.

In an exemplary embodiment, at Stage 1, sample matrix and buffers can be added to the sample cup (e.g., 10 g ground beef in 100 mL DI water). The sample matrix is broken down to millimeter sized particles in about 3 minutes. Particulates less than or equal to 500 μm in buffer are automatically transferred from Stage 1 to Stage 2 where the food matrix homogenizes the sample by cavitation (e.g., about 3 minutes). The homogenized sample matrix is automatically transferred from the cavitation device to Stage 3 where pathogens in the sample are extracted and automatically labeled (e.g., about 90 minutes). Extracted and labeled samples are transferred automatically from Stage 3 to Stage 4 where pathogen bound labels are detected electrochemically (e.g., about 5 minutes).

EXAMPLES

The following examples as set forth herein are intended for illustrative purposes only and are not intended to limit the scope of the disclosure in any way.

Example 1

Bacterial Preparation

In these experiments, the pathogens of *Escherichia coli* and *Cryptosporidium parvum* were prepared. A non-pathogenic variant of *E. coli* O157:H7 was purchased from the American Type Culture Collection (ATCC) in a freeze-dried format and was propagated according to ATCC's instructions. 1 mL of Difco Nutrient broth (Catalog #234000, Becton Dickinson, Sparks. MD, USA) was used to rehydrate the freeze-dried pellet, and this solution was mixed well. Following rehydration, the solution was transferred to a tube containing an additional 5 mL of nutrient broth. A 200 μL aliquot of this solution was spread on an agar plate containing Difco Nutrient Agar (Catalog #213000, Becton Dickinson, Sparks, MD, USA). Both the broth solution and the agar plate were incubated at 37° C. for 24 hours. After propagation, the cultured broth was centrifuged at 1000×g for 10 minutes to concentrate the bacterial cells into a pellet. The supernatant from the broth was removed and the bacteria was resuspended in 3 mL of Difco Nutrient Broth mixed with 20% (vol/vol) sterilized glycerol. The culture was aliquoted in Nalgene Cryogenic vials (Thermo Scientific, Waltham, MA, USA) and stored at −135° C. until ready for use.

To prepare the *E. coli* samples for inoculation, 100 μL of aliquoted *E. coli* solution was spread on a Difco Nutrient Agar plate and incubated for 24 hours at 36° C. A sterile pipette tip was used to scrape a portion of the biofilm and transfer the biofilm into a solution of 1×PBS. *Cryptosporidium parvum* oocysts were diluted using in 1×PBS to achieve the desired concentration.

Cavitation Chamber Preparation

Figure 4:
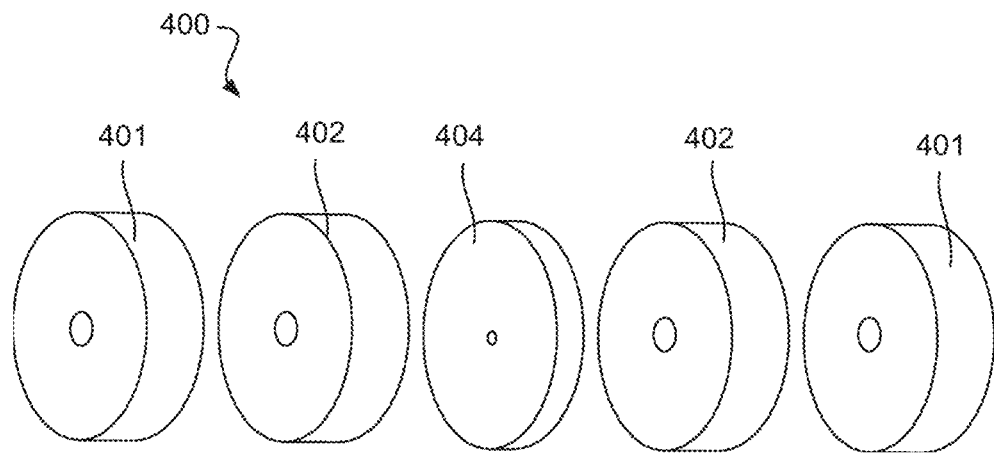
Figure 5A:
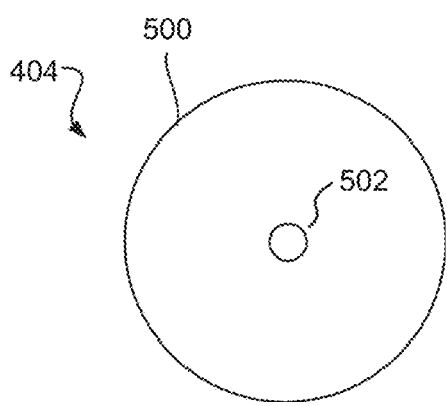
FIG. 5B depicts an example of a back side of the orifice plate of FIG. 5A in accordance with the present disclosure.
Figure 5B:
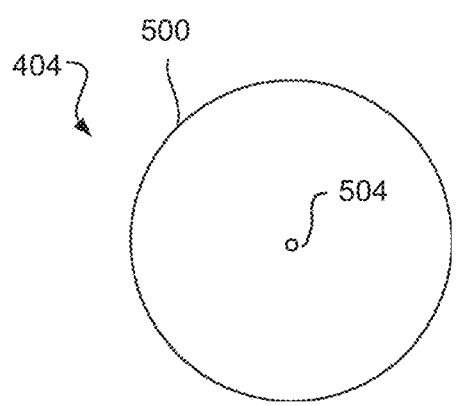

A version of the cavitation chamber depicted in FIGS. 4 and 5 was fabricated using rapid prototyping techniques. In this example, each of the discs is 25 mm acrylic discs was cut out using a Universal Laser Systems versalaser $CO_2$ laser engraving system. These discs were designated for use as either inlet fittings, expansion chambers, or the cavitation orifice plate. The inlet fitting discs and expansion chambers were manufactured with a 1.2 mm diameter channel. The inlet fitting disks were tapped and used to connect the cavitation device to the rest of the system via female Leuer locks. The cavitation orifice plate contained a single 0.8 mm through holes to dramatically reduce the local pressure to which the liquid mixture is exposed. The pressure difference between the expansion chambers and the cavitation orifice plate enabled the creation and destruction of cavitation bubbles in the system.

When the input pressure is too high, the pathogens can be destroyed due to fragmentation (e.g., total rupture of the cell membrane). In some cases, the biosensor used in subsequent testing may not be able to detect fragmented pathogens. Therefore, the cavitation parameters were tested to avoid the total fragmentation of the pathogens while still being aggressive enough to separate pathogens from food particles. In an experiment, *Cryptosporidium parvum* was chosen as the pathogen for optimization of cavitation parameters.

Example 2

For this experiment, four samples containing 40 mm of deionized water spiked with *C. parvum* at 20,000 oocysts/mL were created. Three of these samples underwent a cavitation treatment for seven and a half minutes at input pressures of 8, 14, and 20 PSI respectively. The fourth sample did not undergo the cavitation treatment as a control. After each treatment was applied, anti-*Cryptosporidium* polystyrene beads were attached to the oocysts using methods described above to observe the binding capabilities of *Cryptosporidium* post treatment. Post treatment, 300 μL aliquots of each sample were obtained, and samples were characterized with the use of a BD FACSCanto II flow cytometer. Population side scatter and forward scatter intensities of each sample was recorded concurrently and background scattering intensity due to buffer effects was subtracted. These data were used to quantify the generation of sample debris due to *Cryptosporidium* fragmentation.

In some experiments, flow cytometry revealed no great increase in debris due to the fragmentation of oocysts between samples which had received no cavitation treatment (1230 particulates), samples which had received cavitation conducted at an input pressure of 8 PSI (1794 counts), and samples which received cavitation conducted at an input pressure of 14 PSI (1067 counts). However, samples which received a cavitation treatment with an input pressure of 20 PSI displayed an almost five-fold increase in fragmentation debris observed (5317 counts). Flow cytometry was also used to measure the occurrence of polystyrene bound to oocysts in each aliquot as a percentage of total presence of oocysts in the aliquot. It was observed that increasing the cavitation input pressure reduced the occurrence of oocysts bound to polystyrene beads. Experiments conducted without cavitation had the highest success of bonding with 72% of oocysts bonding to polystyrene beads. The addition of a cavitation treatment resulted in a minor decrease in the occurrence of oocysts bound to polystyrene beads with samples 61% and 60% of oocyst bound in samples that received cavitation at input pressures of 8 PSI and 14 PST, respectively. However, a drastic reduction in binding was observed for samples that received a cavitation treatment with an input pressure of 20 PSI with only 40% of oocysts observed to be bound to polystyrene beads. Due to these results, an input pressure of 11 PSI was chosen for use in future experiments, though it should be appreciated that other input pressures could be used with varying levels of efficiency.

Example 3

In another experiment, eight ground beef samples were inoculated with either *E. coli* ($1.5 \times 10^5$ CFU/mL), *Cryptosporidium* ($2 \times 10^4$ oocysts/mL), or deionized water as a control using the methods described above. After inoculation, the sample received a tenderization pretreatment for one and a half hours and were pre-filtered to collect solids. Samples then either underwent cavitation at 11 PSI for 7 and a half minutes or were left as is. Four 1 mL aliquots of each sample were then collected. Square wave voltammetry scans were performed twice on each aliquot. Scan 1 was used to measure the oxidation of the electrochemical marker used in this experiment, namely polyguanine, while, scan 2 measured the baseline current exhibited by the detector in the absence of oxidation of the electrochemical marker guanine. Scan 2 was subtracted from scan 1 in order to observe the baseline subtracted current exhibited by each sample.

Square wave voltammetry results indicated that the inclusion of hydrodynamic cavitation as a sample preparation step resulted in an increase of electrochemical signal for the samples (i.e., pathogens were detected following hydrodynamic cavitation of the pretreated sample). As expected, blank samples which had not undergone any cavitation treatment exhibited the lowest electrochemical response. A slight increase in electrochemical signal was observed between blank samples which had undergone cavitation and blank samples which did not receive the cavitation treatment. This is likely due to the increased presence of small particulates after the cavitation treatment. These particulates can increase the incidence of detected polystyrene beads non-specifically bound in the system, which in turn increases the electrochemical signal received from a sample. However, even with the blank sample elevated after receiving cavitation, the remaining inoculated samples generally displayed higher electrochemical signals than the blank sample. Post cavitation, a 21.7% increase in signal strength was observe for sample containing *E. coli* and a 19.5% increase in signal strength was observed for samples containing *Cryptosporidium*. It is believed that this indicates that after cavitation is performed an increased number of pathogens were disassociated from the meat particles compared to a treatment of meat tenderization alone.

Example 4

In yet another experiment, three ground beef samples, sample A, B, and C, were inoculated with *E. coli* ($9.8 \times 10^4$ CFU/mL) using the methods described above. After inoculation, the samples were mixed with a solution containing 90 grams of deionized water and 6.6 grams of meat tenderizer (Papain). Samples A and B were placed in a water bath at 70° C. for one and a half hours to allow for the tenderization of meat. Samples C was allowed to rest at room temperature for the same amount of Lime. Sample A was pre-filtered to collect any solids and then underwent cavitation at 11 PSI for 7 and a half minutes. Sample C was processed using through a Seward Stomacher 400 Circulator blender at 230 RPM for 2 minutes and prefiltered to collect any solids. Sample B was pre-filtered and did not receive either a cavitation or stomacher treatment. Four 1 mL aliquots of each sample were then collected.

Pathogenic separation via stomaching displayed several disadvantages compared to cavitation. Stomaching was unable to completely homogenize the sample with 37% of solid sample unable to pass through the filter. Inclusion of a stomaching step resulted in an 30.8% increase of electrochemical signal when compared to a tenderized meat sample that did not undergo cavitation or stomaching. However, the inclusion of cavitation resulted in a 37% increase in electrochemical signal when compared to a tenderized meat sample. This indicates that cavitation's ability to separate pathogenic material embedded in meat is greater than what can be observed with the use of a stomacher.

Electrochemical detection of an electrochemical maker, in this case polyguanine, was performed. A solution containing 1 mL of sample and 10 µL of magnetic beads were added to a 1.7 mL microcentrifuge tube. This solution was then allowed to mix end over end at 32 rpm for 40 minutes. After mixing, the microcentrifuge tube was placed in a custom-made magnetic rack with N42SH neodymium magnets to carry out the immunomagnetic separation process. The tube remained on the magnetic rack for three minutes, being inverted once per minute. After three minutes the supernatant from each tube was then discarded and 1 mL of PBS wash buffer was added. This process is repeated twice to ensure the washing of any non-target particles in the system.

Following immunomagnetic separation, 15 µL of dual conjugated polystyrene beads were added to the solution. This solution was then allowed to mix end over end for another 40 minutes. After 40 minutes, each tube was once again placed on the custom magnetic rack for three minutes, being inverted once per minute, and then the supernatant was discarded, and 1 mL of polystyrene beads wash buffer is added. This process was repeated two times to wash unbound polystyrene beads out of the system.

To elute the electrochemical marker (i.e., polyguanine) from the polystyrene beads, the supernatant was removed from the solution and 250 µL of an elution buffer containing equal parts of a 95% formamide, diluted with DNase/RNase free water, and an 80 mM NaOAc, diluted in DNase/RNase free water, was added. The tubes were then put into a water bath held at 90° C. for 10 min. Each sample was then transferred to a well on the Dropsens 96 well screen-printed carbon electrode plate. The supernatant was allowed to adsorb on the electrode plate for ten minutes. After 10 minutes, square wave voltammetry was carried out on the electrodes using the parameters listed in Table 1. Square wave voltammetry is conducted twice per well and the resulting current measurements are recorded.

TABLE 1

| Setting | Value |
| --- | --- |
| Equilibrium time | 8 seconds |
| Starting potential | 0.34 Volts |
| Ending potential | 1.2 Volts |
| Step potential | 0.005 Volts |
| Amplitude | 0.02 Volts |
| Frequency | 100 Hertz |
| Reverse Scan | N/A |

Example 5

Virus Detection in Strawberries Using Cavitation and PCR

The following data set includes virus concentration between 1e4 and 1e6 inoculated on strawberries. The current standard method is shaking the berries in an elution buffer, collecting the virus, and running real-time polymerase chain reaction for virus detection. The control in these experiments is virus in PBS at the same amount as what is inoculated on berries.

The samples with lower Ct values on PCR indicate the presence of more virus in sample when compared to the samples with lower Ct values. Our data shows better virus recovery (lower Ct value) when the sample is subjected to hydrodynamic cavitation compared to just shaking which is used as gold standard method.

Reagents include DI water, Tris base (Fisher Bioreagents catalog #BP154-1), Glycine (Fisher Chemical catalog #G46-1), Beef extract powder (Acumedia catalog #LS-1061241), and Norovirus: Sydney NV 14-096 CT 23.

Materials include stomacher bag with 0.5 mm filter, stomacher bag rack, Talboys advanced orbital shaker, cavitation device with 1.9 mm orifice diameter.

The TGBE Elution buffer is prepared as follows:

1. Mix:
   a. Tris Base (18.15 g)
   b. Gylcine (5.7 g)
   c. Beef extract (15 g)
   d. DI water (1500 mL)
2. Adjust pH of your elution buffer to 9.5±0.2 using NaOH
   a. Roughly 30 mL of NaOH should get it to 9.59 (we were able to get our buffer to 9.544)
3. Autoclave buffer for 20 minutes at 121° C.
4. Let buffer cool.

The strawberries were cleaned as follows:

1. In a weigh boat, measure out strawberries at ~20-25 g (we measured samples between 21-23 G)
2. Put strawberries in BSL-2 fume hood
3. Irradiate with UV light for 5 minutes to sterilize surface of the strawberries
4. Rotate the strawberries by at least 60° C. (up to 90° C.)
5. Repeat steps 3 and 4 two times
6. Let strawberries rest for up to 5 minutes Six samples of strawberries were prepared: Negative control elution only, Negative control elution+cavitation, High concentration elution only, High concentration elution+cavitation, Low concentration elution only, and Low concentration elution+cavitation. Each of these samples contained ~25 grams of strawberries. Samples designated as negative control received a 200 μL inoculation of just sterile PBS buffer. Samples designated as High concentration received a 200 μL inoculation of a $10^{-1}$ dilution of norovirus (roughly $10^5$ viruses per μL of solution or $2\times10^7$ viruses on the surface of the strawberries). Samples designated as low concentration received a 200 μL inoculation of a $10^{-3}$ dilution of norovirus (roughly 10 viruses per μL of solution or $2\times10^5$ viruses on the surface of the strawberries). Strawberries received inoculation by placing small drops randomly over the surface of the strawberry and letting it rest in the fume hood for at least 30 minutes.

Positive and negative controls were also added to our sample. A D1 positive control includes 200 μL of the $10^{-1}$ dilution of norovirus. A D3 positive control includes 200 μL of the $10^{-3}$ dilution of norovirus. A PBS negative control includes 200 μL of sterile PBS. Each of the foregoing controls were mixed with 50 mL of elution buffer prior to the elution step.

The viruses were eluted from the strawberries as follows: all strawberry samples were transferred to a stomacher bag with a 0.5 mm filter. Elution buffer was added to a total weight of 150 g of sample. Placed all samples on a stomacher bag holder rack and ensured sure all the strawberries were completely submerged in the elution buffer before rotation. Controls were also transferred to stomacher bags after diluting to a total volume of 150 mL in elution buffer. The loaded stomacher rack was placed on an orbital shaker and shaken at 150 rpm for 1 hour at room temperature. Samples that simply needed to be eluted were ready to go to the precipitation step. Samples undergoing cavitation followed the protocol below.

Cavitation of elution buffer was performed by cavitating the liquid part of the sample—without removing the filter bag—for 7.5 minutes at a gear pump setting of 90, generating a pressure of about 25 PSI with a cavitation device having a 1.9 mm cavitation orifice.

Precipitation of viruses from the fluid was performed as follows:

1. Collected 39 mL of eluted or cavitated sample.
2. Adjusted the PH to 7.0 (about 2 mL of a 2 N HCl).
3. Separated bulk particles from any suspended pathogens by centrifuging @ 3000 RCF for 15 minutes.
4. Transferred the elute to another tube, while avoiding transfer of bulk solids.
5. Added a peg precipitate solution to the elute at a 1:1 ratio for a 1× peg solution containing 1% BSA (Dnase, RNAse, protease free), 12% PEG, and 0.9 M NaCl.
6. Incubated sample and PEG for at least 2 hour at 4° C.
7. Centrifuged at 10,000×g for 20 minutes at 8° C.
8. Removed the supernatant while ensuring not to disturb the pellet.
9. Added 800 μL of PBS to each sample. Vortexed vigorously for 10 seconds to ensure mixing.
10. Clarified the sample via a chloroform-butanol extraction (e.g., adding 400 μL of butanol and 400 μL of chloroform to a 800 μL sample).
11. Vortexed samples for 2 minutes.
12. Centrifuged at 12,000×g for 10 minutes.
13. Recovered the aqueous phase.
14. Stored at −80° C. until RNA extraction and RT-PCR.

The RT-PCR data from the above samples are illustrated in FIG. 14.

Example 6

Six samples of blackberries were prepared: Negative control elution only, Negative control elution+cavitation, High concentration elution only, High concentration elution+cavitation, Low concentration elution only, and Low concentration elution+cavitation. Each of these samples contained ~25 grams of blackberries. Samples designated as negative control received a 200 μL inoculation of just sterile PBS buffer.

Samples designated as High concentration received a 200 μL inoculation of a $10^{-1}$ dilution of norovirus (roughly 10 viruses per μL of solution or $1\times10^6$ viruses on the surface of the blackberries) and a 100 μL inoculation of a $10^{-1}$ dilution of Hepatitis A virus (roughly $1\times10^7$ RT-PCRU of viruses on the surface of the blackberries).

Samples designated as low concentration received a 200 μL inoculation of a $10^{-3}$ dilution of norovirus (roughly $10^3$ viruses per μL of solution or $2\times10^5$ viruses on the surface of the strawberries). Samples designated as low concentration received a 100 μL inoculation of a $10^{-3}$ dilution of norovirus (roughly $10^2$ viruses per μL of solution or $1\times10^4$ viruses on the surface of the blackberries) and a 100 μL inoculation of a $10^{-3}$ dilution of Hepatitis A virus (roughly $1\times10^5$ RT-PCRU of viruses on the surface of the blackberries) Blackberries received inoculation by placing small drops randomly throughout the surface of the blackberry and letting it rest in the fume hood for at least 1 hour.

Positive and negative controls were added, including a DI positive control, which is 100 μL of $10^{-1}$ dilution of norovirus and 100 μL of $10^{-1}$ dilution of Hepatitis A virus; a D3 positive control, which is 100 μL of $10^{-3}$ dilution of norovirus and 100 μL of $10^{-3}$ dilution of hepatitis A virus; and a PBS negative control, which is 200 μL of sterile PBS. These controls were mixed with 50 mL of elution buffer prior to the elution step and processed above, as in Example 5.

Figure 15A:
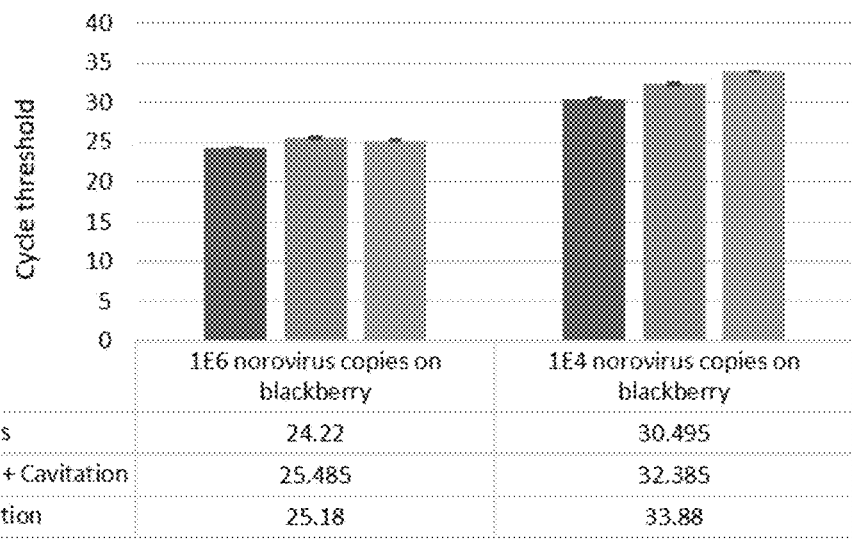
FIG. 15A is a graph illustrating results of detecting a virus in a sample of blackberries using cavitation methods and systems in accordance with the present disclosure.
Figure 15B:
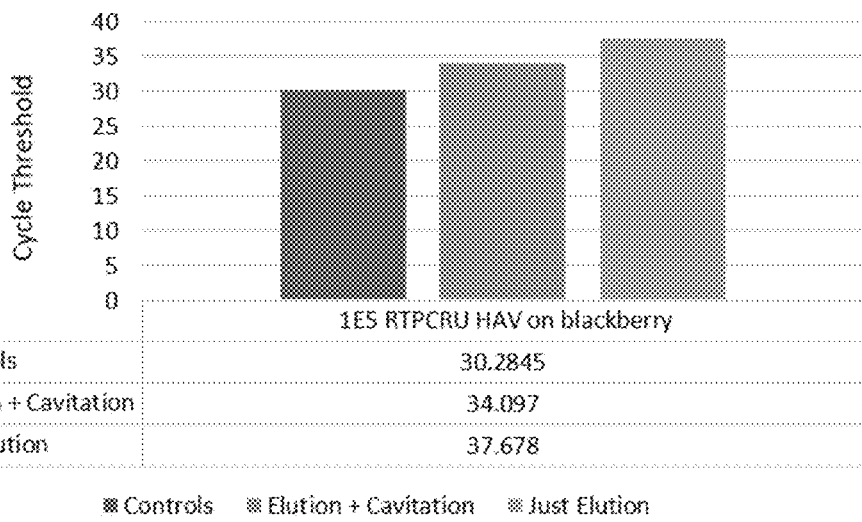
FIG. 15B is a graph illustrating results of detecting a virus in a sample of blackberries using cavitation methods and systems in accordance with the present disclosure.

These data, illustrated in FIGS. 15A and 15B show that the Hepatitis A virus, which is sticky in nature, cannot usually be detected at 10,000 virions in 1 mL as Ct value is over 37. The use of cavitation allows detection of these viruses that would otherwise remain undetected, as indicated by the Ct value of 34, which is much closer to control Ct values.

It should be appreciated that the systems and methods illustrated herein can additionally incorporate chemical degradation.

Example 7

Due to the need for viable stem cells that can be used in clinical trials a device was created that uses a mechanical process to separate and break down adipose tissue. The stem cells need to be separated into the Stromal Vascular Fraction (SVF) with a high cell viability and be quickly and easily removed in an operating room environment.

Using a single orifice cavitation system, as described herein, we saw bubble formation in the range of 470-600 mL/min; the peristaltic pump tubing used is only rated for 480 mL/min so further testing was limited to less than 480 mL/min.

The fat reduction testing involved three critical steps; fat liquidation, fat processing, and fat observation.

Fat Liquidation: In order to obtain samples that we could run through our device the fat had to be reduced to an almost liquid state. The fat being used was pig fat from a local deli, this fat was completely solid and not able to be processed with our device. Liquidation involved scraping a razor across the surface and collecting the gelatin like substance that formed on the edge of the razor. This was a long and arduous process, but we are anticipating that the fat that will be used in our device will already be in a semi-liquid state.

Fat Processing: Involved treating the fat with our cavitation device. The liquidated fat was weighed and placed in a single sample of water at a fifty-to-one water to fat ratio. This sample was constantly stirred to achieve a homogenous mixture. This fat and water mixture was then divided into 3 equal containers. A control sample of sample of each test sample was created for observation. Each container would be processed at a different pump speed; 2.5, 5, and 7.5 being the respective peristaltic pump speeds. Each sample was then subjected to a treatment with the cavitation device. The first treatment involved running the full sample once through the cavitation device. The second test was to run the sample through four complete cycles. The third test was to run the same sample with a continuous circulation for 90 seconds. After each respective test a sample was prepared for observation.

Fat Observation: Observation consisted of placing each prepared sample under the microscope and observing the fat cells at three random locations per sample. The data sheet recorded three main groups, and an average value was taken for each sample. Clumps: any group of two or more cells clearly attached with one another. Singles: Any single fat cells standing alone measuring about 2 microns. Smalls: Any object smaller than the average fat cell diameter of 2 microns.

The results indicate an overall reduction in the size of the treated fat cells compared to the control fat cells. Controls samples all contained large amounts of clumps, or single large clumps of cells with few single cells and no small specimens. After treatment the overall reduction in clump sizes was greatly reduced and small specimens began to appear. After the most extreme treatments no clumps were visible, and most visible specimens were small specimens under 2 microns indicating that the cavitation nozzle indeed has the ability to break down cells.

To understand the effects of the device on living cells, *E. coli* were passed through the device at three different flow rates and cultured after a single pass. Five controls were cultured for the experiment. The first two were directly from the diluted bacterial solution to determine a rough count of bacteria to be expected. The other three were from a 0.02 mL bacterial to 1 mL of deionized water solution that had only been pumped through the peristaltic pump at the three different flow rates, to determine if the pump was killing the bacteria. Finally, 3 solutions of 0.02 mL bacterial to 1 mL of deionized water were mixed and passed through the device at rates of 160 mL/min, 320 mL/min, and 470 mL/min. The bacteria were cultured over a 24-hour period.

From this test it has been concluded that the device does not kill the bacteria and are unlikely to kill stem cells, making the device operable for stem cell isolation.

CONCLUSION

The cavitation parameters are adjusted so as to not fragment the pathogens of interest. This fine tuning of the cavitation device may allow for the hydrodynamic cavitation technique to be compatible with several downstream analytic methods, such as electrochemical detection methods. In some examples, flow cytometry revealed no significant increase in debris due to the fragmentation of *C. parvum* oocysts between samples which had received no cavitation treatment (983 counts), samples which had received cavitation conducted at an input pressure of 8 PSI (55.2 kPa, 1427 counts), and samples which received cavitation conducted at an input pressure of 14 PSI (96.5 kPa, 1250 counts). However, samples which received a cavitation treatment at an input pressure of 20 PSI (137.9 kPa) displayed an almost three-fold increase in debris observed (3321 counts). A one-way ANOVA was conducted to compare the effects of cavitation on the generation of *C. parvum* debris. It is observed that there was no significant difference in the amount of *C. parvum* debris generated when cavitation is performed at 14 PSI or below compared to when there is no cavitation performed at all. For input pressures of 14 PSI and below the increase in debris due to cavitation was not significant within a 99% confidence interval with $p>0.7024$ for 8 PSI and $p>0.9103$ for 14 PSI. However, when the pressure is increased in some examples above 14 PSI, a significant difference in the amount of *C. parvum* debris was observed within a 99% confidence interval with $p<0.0019$.

In some examples, flow cytometry was used to measure the incidence of polystyrene beads bound to *C. parvum* oocysts in each aliquot as a percentage of total presence of *C. parvum* oocysts in the aliquot. The antibody conjugated to the polystyrene beads was raised for the detection of epitopes on the outer wall of *C. parvum* oocysts. This antibody does not efficiently attach to *C. parvum* oocysts walls that have been fragmented and damaged. Therefore, the number of polystyrene beads bounded to *C. parvum* was used as a secondary indicator of *C. parvum* oocyst fragmentation. It was observed in some examples that increasing the cavitation input pressure reduced the occurrence of *C. parvum* oocysts bound to polystyrene beads. Experiments conducted without cavitation had the highest success of bonding with 72% of *C. parvum* oocysts bonding to polystyrene beads. The addition of a cavitation treatment resulted in a minor decrease in the occurrence of *C. parvum* oocysts bound to polystyrene beads with 61% and 60% of *C. parvum* oocysts bound in samples that receive cavitation at input pressures of 8 PSI and 14 PSI, respectively. However, a drastic reduction in binding was observed in some examples for samples which received a cavitation treatment with an input pressure of 20 PSI. In these examples, only 40% of *C. parvum* oocysts present in samples that received cavitation at an input pressure of 20 PSI were observed to be bound to polystyrene beads, which is believed to suggest that cavitation pressure above 14 PSI resulted in the fragmentation of *C. parvum* oocysts. While these experiments correlated with better results at some cavitation pressures, under different cavitation device parameters, other cavitation pressures may cause different results. Any appropriate activation pressure may be used in accordance to the principles described in this disclosure.

Figure 9:
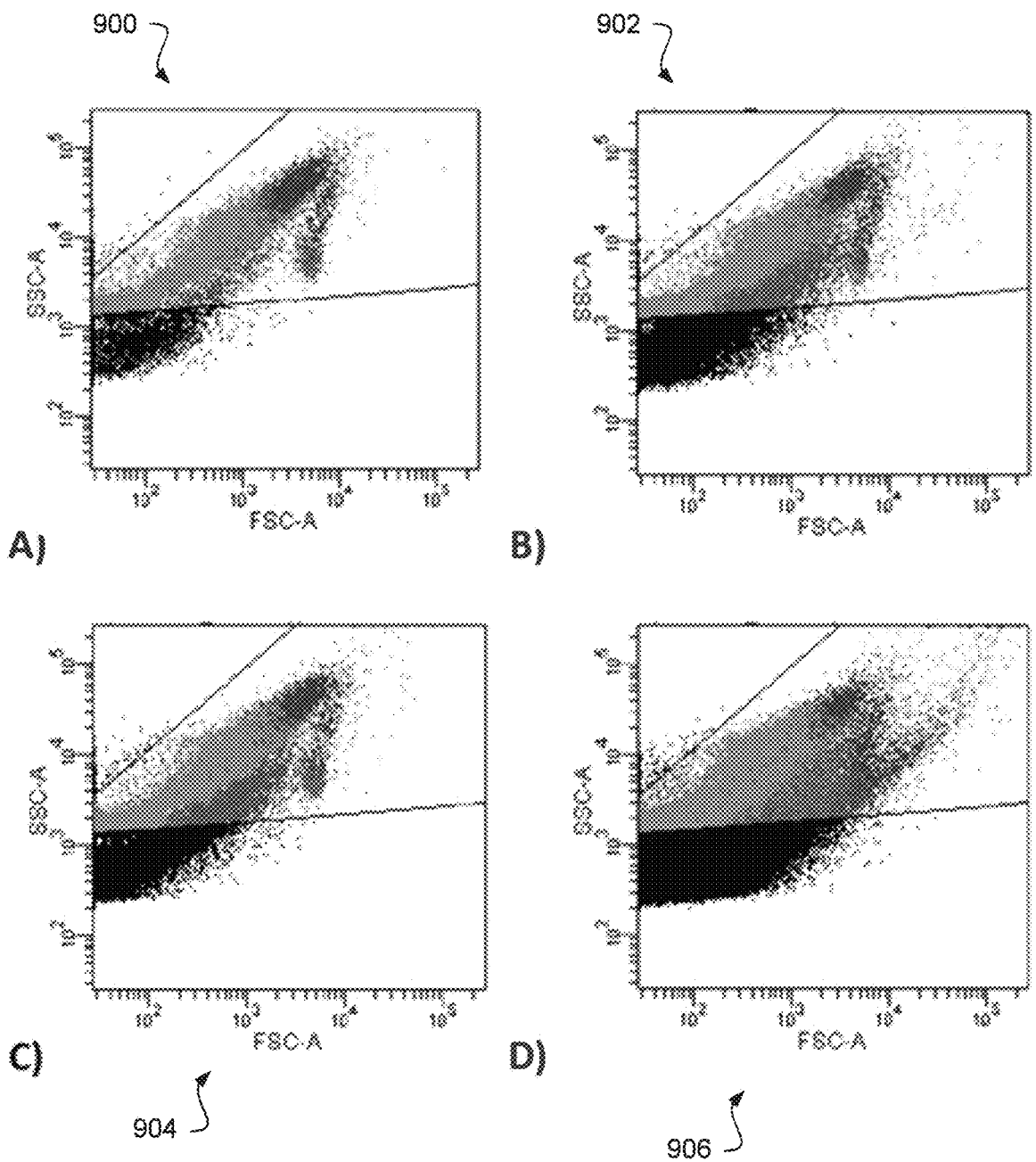
FIG. 9 depicts forward scatter versus side scatter plots of samples containing oocysts (blue), polystyrene beads (orange), anti-*Cryptosporidium* magnetic beads (purple), oocyst debris (red), and background debris (black) as observed in some examples via flow cytometry in accordance with the present disclosure.

FIG. 9 depicts a population forward scatter vs. side scatter of samples containing *C. parvum* oocysts (blue), polystyrene beads (orange), anti-*Cryptosporidium* magnetic beads (purple), *C. parvum* oocyst debris (red), and background debris (black) as observed in some examples via flow cytometry. Sample 900 received no cavitation; sample 902 received cavitation at an input pressure of 8 PSI; sample 904 received cavitation at an input pressure of 14 PSI; and sample 906 received cavitation at an input pressure of 20 PSI.

Without being limited to any one theory, the results of these experiments are believed to have shown the results of the combination of hydrodynamic cavitation and enzymatic digestion for the separation of pathogens from a food item such as a meat. In some examples, this process includes a pretreatment of the food product, and in the case of meat, using enzymatic digestion. While the pretreatment performed in some of these examples using meat resulted in a semi-liquid solution of beef, fat, and collagen, it was unclear whether this solution alone would facilitate maximum recovery of pathogens or whether further processing was needed. A comparison was made between meat samples which had only received enzymatic digestion and meat samples that underwent both cavitation and enzymatic digestion. Square wave voltammetry results indicate that the inclusion of hydrodynamic cavitation as a sample preparation step results in the increase of electrochemical current response for all samples. A summary of the results can be found in Table 2.

TABLE 2

Effect of Cavitation on Electrochemical signal

| Inoculant | Pathogen Inoculation | Cavitation Treatment | Mean Current (µA) | Sample SD | CV (%) |
|---|---|---|---|---|---|
| E. coli | − | − | 2.89 | ±0.11 | 4 |
|  | − | + | 3.18 | ±0.23 | 7 |
|  | + | − | 3.29 | ±0.54 | 16 |
|  | + | + | 3.87 | ±0.08 | 2 |
| C. parvum | − | − | 2.34 | ±0.18 | 8 |
|  | − | + | 2.41 | ±0.33 | 14 |

TABLE 2-continued

Effect of Cavitation on Electrochemical signal

| Inoculant | Pathogen Inoculation | Cavitation Treatment | Mean Current (µA) | Sample SD | CV (%) |
|---|---|---|---|---|---|
|  | + | − | 2.56 | ±0.28 | 11 |
|  | + | + | 2.88 | ±0.07 | 2 |

Without being limited to any one theory, these square wave voltammetry results are believed to suggest that cavitation resulted in an increase in the baseline electrochemical response for uninoculated samples. Those samples that were neither inoculated with a pathogen nor underwent any cavitation treatment exhibited the lowest current response, 2.89±0.11 pA for *E. coli* tests and 2.34±0.18 pA for *C. parvum* tests, respectively. An at least 3% increase in current response was observed in some examples between uninoculated samples which underwent cavitation and uninoculated samples which did not receive the cavitation treatment, 3.18±0.23 pA for *E. coli* tests and 2.41±0.33 pA for *C. parvum* tests, respectively. This increase may be due to the increased presence of small particulates after the cavitation treatment as shown in the flow cytometry results. These particulates can increase the incidence of polystyrene beads non-specifically bound in the system, which in turn may increase the electrochemical signal received from a sample. However, all inoculated samples still display higher electrochemical signals than the uninoculated samples.

In some cases, samples that were inoculated by pathogens also generated higher electrochemical responses after receiving the cavitation treatment. The cavitation treatment resulted in a 17.6% increase in the current response observed in some examples for samples containing *E. coli* and a 12.5% increase in signal strength was observed for samples containing *C. parvum* when compared against inoculated samples which did not receive cavitation. A one-way ANOVA was conducted to compare the effects of cavitation on the electrochemical signal. For both pathogens, the increase in electrochemical signal due to cavitation was significant within a 90% confidence interval with $p<0.0733$ for *C. parvum* and $p<0.0465$ for *E. coli*. Additionally, a significant difference was also observed in some examples between inoculated meat samples which only received tenderization pretreatment and meat which receive both tenderization and cavitation, $p<0.0999$ for *E. coli*. This is believed to indicate that the combination of tenderization pre-treatment and cavitation disassociated pathogens from meat particles better than meat tenderization alone.

Figure 10:
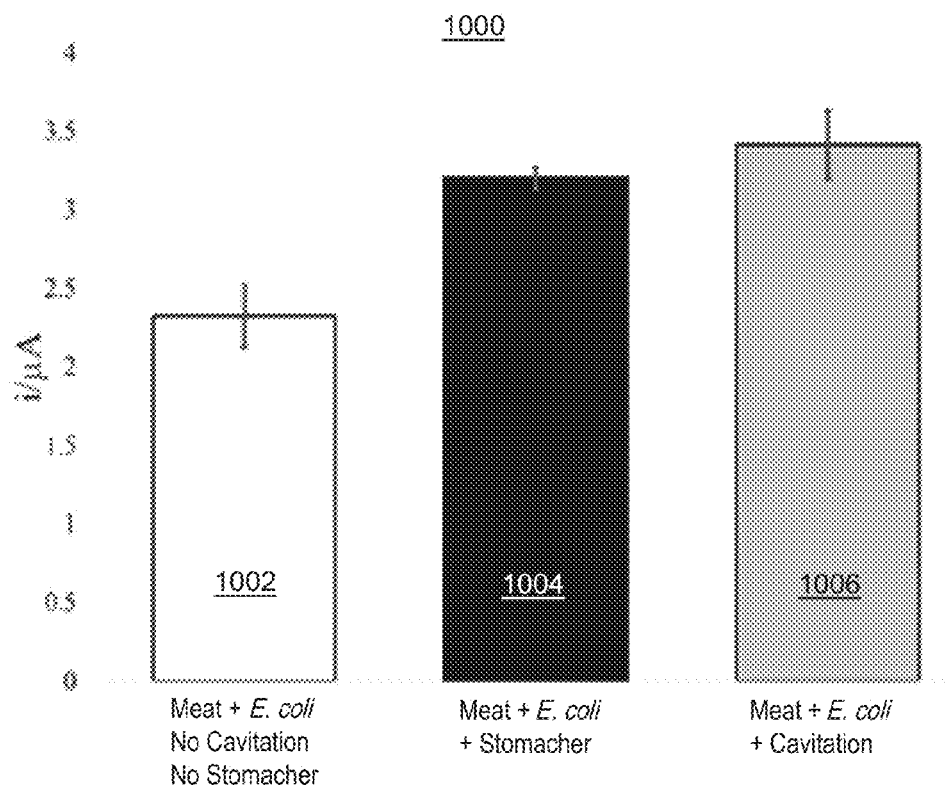
FIG. 10 depicts a comparison of electrochemical responses generated by inoculated samples in accordance with the present disclosure.

A comparison between pathogenic separation via hydrodynamic cavitation and pathogenic separation via stomaching was also made. FIG. 10 depicts a comparison of electrochemical responses generated by inoculated samples which received the cavitation treatment verses inoculated samples which solely received a stomaching treatment using a stomacher. In this depiction, the y-axis 1000 represents electrical current. The first bar 1002 represents meat and *E. coli* that have not undergone a process through the cavitation device nor through the stomacher. The second bar 1004 represents meat and *E. coli* that has undergone just a stomaching process through the stomacher. The third bar 1006 represents meat and *E. coli* that has undergone just a process through the cavitation device.

In some examples, square wave voltammetry results are believed to have indicated that the inclusion of hydrodynamic cavitation in sample preparation may result in an increase of electrochemical current response when compared with stomacher samples. In some examples, samples which only received a tenderization treatment displayed a current response of 2.336±0.203 µA. Samples which received only the stomacher treatment generated a current response of 3.201±0.071 µA. Also, samples which received both the tenderization treatment and hydrodynamic cavitation treatment displayed a current response of 3.415±0.221 µA. A one-way ANOVA was conducted to compare the effects of stomaching and cavitation on the electrochemical signal. Both cavitation and stomaching significantly increased the electrochemical response of the sensor within a 99% confidence interval, with $p<3.20\times10^{-5}$ for cavitation and $p<1.80\times10^4$ for stomaching. A comparison between stomaching and cavitation in some examples showed that they elicit nearly similar current responses for the electrochemical sensor, with $p=0.25$. These results are believed to have illustrated that at least some cavitation techniques are least equivalent to the stomacher approach and can be used as an alternative method for detaching pathogens embedded in a food product such as ground beef.

In some examples, pathogenic separation via stomaching displayed several disadvantages when compared to cavitation. Samples that received both the pretreatment and cavitation were almost completely homogenized. Greater than 90% of the samples that received this treatment easily flowed through the downstream sample filter. However, stomaching was unable to completely homogenize the sample, with 42.9% of the stomached sample unable to pass through the sample filter. Additionally, stomaching of ground meat samples generated a considerable amount of debris. This makes stomaching incompatible with techniques such as PCR due to an efflux of PCR inhibitors such as fat and several proteins from the meat. Cavitation had the potential to degrade such PCR inhibitors, negating this need for further sample preparation steps before PCR was performed on ground meat samples. Additionally, in some cases, stomaching was a batch process and was not combined with any inline detection or sample processing units. The hydrodynamic cavitation system used in this work was a semi-batch process, which allowed for the automated introduction of new samples and removal of processed samples using a mechanism such as three-way valves. These advantages may make hydrodynamic cavitation a suitable option for semi-continuous monitoring of commercial foodstuffs.

These experiments are believed to show that the electrochemical detection of pathogens embedded in ground beef prepared using hydrodynamic cavitation can be used as a pathogen release technique. Cavitation parameters were chosen to allow the aggressive homogenization of meat while preventing total fragmentation of pathogens. Hydrodynamic cavitation is believed to have shown an increase in the electrochemical signal obtained from meat samples containing both *E. coli* and *C. parvum*, suggesting that more pathogens were released and detected when compared to samples prepared using the stomacher or without cavitation. Accordingly, the use of hydrodynamic cavitation was shown to be a viable alternate for separation of embedded pathogens in meat when compared to a Seward stomacher blender.

Figure 11:
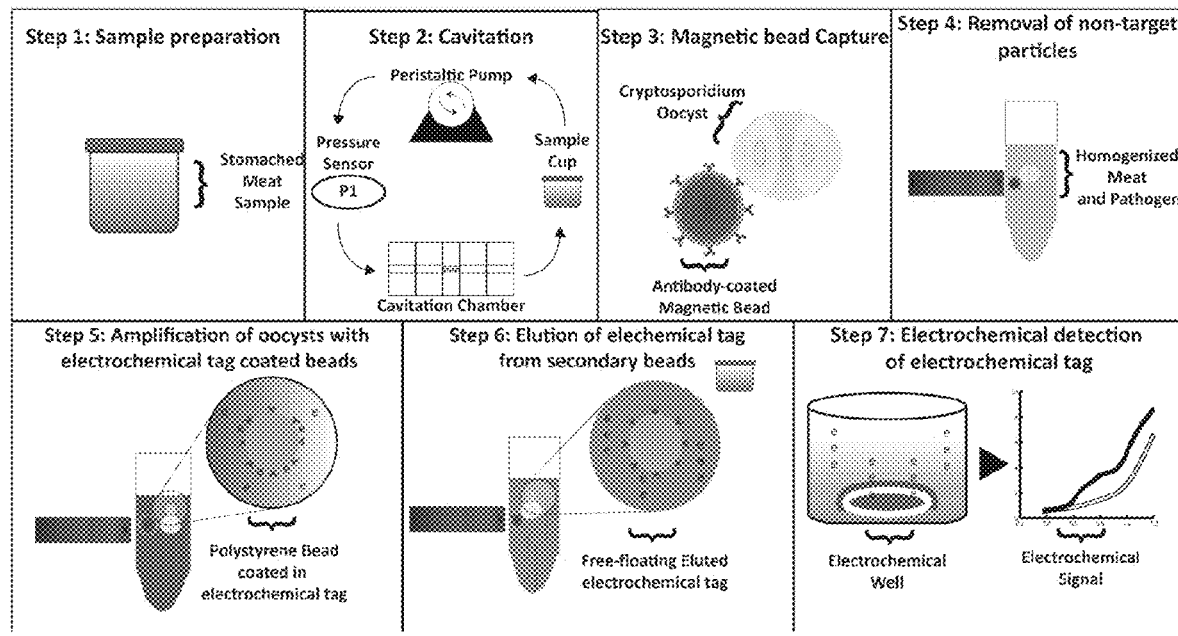
FIG. 11 depicts an example of the tasks involved with carrying out a test to detect the presence and/or concentration of a pathogen in accordance with the present disclosure.

An example of the tasks involved with carrying out a test to detect the presence and/or concentration of a pathogen is depicted in FIG. 11. In this example, the method includes a pretreatment of a meat, cavitation of the pretreated meat, magnetic bead capture, removal of non-target particles, amplification of oocysts with polyguanine coated beads, elution of polyguanine from secondary beads, and electrochemical detection of polyguanine.

While the examples above have been described with specific materials, purchased devices, and various parameters for each of these experiments, the principles contained herein may include variations from the specific materials, purchased devices, and various parameters included in these experiments. Any appropriate materials, test equipment, or other types of parameters may be used to carry out the principles disclosed herein.

While multiple experiments and their results were presented herein, the results of these experiments are dependent on the parameters and the conditions under which these experiments were conducted. While certain theories for these results of these experiments may be expressed herein, Applicant does not intend to be bound by any particular theories.

What is claimed is:

1. An apparatus for sample preparation, comprising:
a fluid circuit;
a filter loop, wherein the filter loop is incorporated into the fluid circuit;
a directional control valve configured to selectively direct fluid into the filter loop;
a cavitation chamber incorporated into the fluid circuit, the cavitation chamber including:
a channel;
a first cross-sectional area of the channel;
a second cross-sectional area of the channel, wherein the second cross-sectional area of the channel is smaller than the first cross-sectional area and oriented downstream from the first cross-sectional area with respect to fluid flow through the fluid circuit;
a third cross-sectional area of the channel, wherein the third cross-sectional area of the channel is larger than the second cross-sectional area and oriented downstream from the second cross-sectional area with respect to fluid flow through the fluid circuit, wherein the third cross-sectional area of the channel is also larger than the first cross-sectional area;
a pump in fluid communication with the cavitation chamber; and
a pressure sensor associated with the fluid circuit and positioned upstream of the cavitation chamber,
wherein the apparatus is configured to force a liquid mixture through the cavitation chamber at a pressure that separates pathogens from particles in the mixture without fragmenting at least 30% of the pathogens; and
wherein the directional control valve is configured to selectively direct fluid into the filter loop or a cavitation loop including the cavitation chamber.

2. The apparatus of claim 1, wherein the second cross-sectional area is formed by at least a first orifice defined in a cavitation plate disposed within the cavitation chamber.

3. The apparatus of claim 2, wherein the third cross-sectional area is formed by an aperture defined by an expansion plate disposed downstream of the cavitation plate within the cavitation chamber.

4. The apparatus of claim 2, wherein the first orifice has a cross-sectional width that is between 0.5 mm and 1.5 mm.

5. The apparatus of claim 2, wherein the first orifice has a cross-sectional width of about 0.8 mm and the first cross-sectional area of the channel that is upstream from the first orifice has a cross-sectional width of about 1.2 mm.

6. The apparatus of claim 1, wherein the second cross-sectional area is formed by at least a first orifice and a second orifice defined in the cavitation plate,
wherein the first orifice is spaced apart away from the second orifice at a distance, and wherein the first orifice and the second orifice allow a liquid to flow through the cavitation plate in parallel.

7. The apparatus of claim 6, wherein the first orifice has a cross-sectional width less than 1.0 mm and an aperture downstream from the first orifice into which the liquid mixture enters after flowing through the first orifice has a cross-sectional width greater than 1.0 mm.

8. The apparatus of claim 7, wherein the cross-sectional width of the first orifice is about 0.8 mm and the cross-sectional width of the aperture is at least 1.2 mm.

9. The apparatus of claim 1, further comprising a filter incorporated into the filter loop.

10. The apparatus of claim 9, wherein the filter is a tangential flow filter.

11. The apparatus of claim 1, further comprising a cavitation loop including the cavitation chamber wherein the directional control valve is configured to selectively direct fluid into the cavitation loop or into the filter loop.

12. The apparatus of claim 1, wherein the apparatus is configured to force a liquid mixture through the cavitation chamber at a pressure that separates pathogens from particles in the mixture without fragmenting at least 50% of the pathogens.

13. The apparatus of claim 1, wherein the apparatus is configured to force a liquid mixture through the cavitation chamber at a pressure of 5-20 PSI.

14. The apparatus of claim 1, wherein the apparatus is configured to force a liquid mixture through the cavitation chamber at a pressure that separates pathogens from particles in the mixture without fragmenting at least 75% of the pathogens.

15. The apparatus of claim 14, wherein the apparatus is configured to force a liquid mixture through the cavitation chamber at a pressure of 8-14 PSI.

16. The apparatus of claim 1, wherein the apparatus is configured to force a liquid mixture through the cavitation chamber at a pressure that separates pathogens from particles in the mixture without fragmenting at least 90% of the pathogens.

17. The apparatus of claim 16, wherein the apparatus is configured to force a liquid mixture through the cavitation chamber at a pressure of 8-14 PSI.

18. The apparatus of claim 17, wherein the apparatus is configured to force a liquid mixture through the cavitation chamber at a pressure of about 11 PSI.

19. The apparatus of claim 1, wherein the second cross-sectional area is formed by a single orifice defined in the cavitation plate, wherein the cross-sectional width of the single orifice is about 0.8 mm and the first cross-sectional area of the channel that is upstream from the first orifice has a cross-sectional width of about 1.2 mm.

20. The apparatus of claim 1, wherein the filter loop includes a discharge mechanism.

21. The apparatus of claim 20, wherein the pump provides a different input pressure when the fluid is directed through the filter loop as compared to when the fluid is directed through the cavitation loop.

22. A method for detecting a pathogen in a food substance, comprising:
- breaking down solids in the food substance to create a liquid mixture;
- fluidically coupling the liquid mixture to the apparatus of claim 11;
- filtering the liquid mixture via the filter; and
- separating the pathogen from the filtered, liquid mixture without fragmenting at least 30% of the pathogens by forcing the liquid mixture through the cavitation chamber.

23. The method of claim 22, wherein breaking down solids is achieved with an enzyme.

\* \* \* \* \*